US008680045B2

(12) United States Patent
Primiano et al.

(10) Patent No.: US 8,680,045 B2
(45) Date of Patent: Mar. 25, 2014

(54) COMPOSITIONS OF A PEPTIDE TARGETING SYSTEM FOR TREATING CANCER

(75) Inventors: Thomas Primiano, Monona, WI (US); Bey-Dih Chang, Madison, WI (US); Jeremy Heidel, Madison, WI (US)

(73) Assignee: PeptiMed, Inc., Madison, WI (US)

( * ) Notice: Subject to any disclaimer, the term of this patent is extended or adjusted under 35 U.S.C. 154(b) by 0 days.

(21) Appl. No.: 13/287,110

(22) Filed: Nov. 1, 2011

(65) Prior Publication Data

US 2012/0208742 A1 Aug. 16, 2012

Related U.S. Application Data

(60) Provisional application No. 61/456,127, filed on Nov. 1, 2010.

(51) Int. Cl.
*A61K 38/02* (2006.01)
*C07H 21/04* (2006.01)

(52) U.S. Cl.
CPC ..................................... *A61K 38/02* (2013.01)
USPC ............ 514/1.2; 530/300; 530/350; 530/324; 536/23.1

(58) Field of Classification Search
None
See application file for complete search history.

(56) References Cited

U.S. PATENT DOCUMENTS

2010/0119529 A1* 5/2010 Furgeson et al. .......... 424/181.1

FOREIGN PATENT DOCUMENTS

| EP | 1752536 A1 | 2/2007 | |
|---|---|---|---|
| WO | 200125422 A2 | 4/2001 | |
| WO | 2005116204 A1 | 12/2005 | |
| WO | WO2007002362 * | 1/2007 | ........... A61K 39/395 |
| WO | 2007045243 A2 | 4/2007 | |
| WO | 2007134245 A2 | 11/2007 | |

OTHER PUBLICATIONS

Chemical formula for K8-ELP(160)—http://www.springerimages.com/Images/Biomedicine/1-10.1007_s11095-007-9382-5-0; accessed Nov. 28, 2012.*
Meade, Bryan R. et al "Enhancing the cellular uptake of siRNA duplexes following noncovalent packaging with protein transduction domain peptides" (Mar. 1, 2008) Adv Drug Deliv. Rev. 60(4-5): 530-536.*
The Twenty Natural Amino Acids chart, http://wayback.archive.org/web/*/http://chemistry.caltech.edu/groups/dad/ch41/amino_acids.pdf, online version from Jun. 16, 2004; accessed Dec. 13, 2012.*
Raveh, S. et al. "Mini-review: L1 cell adhesion molecule (L1CAM) in invasive tumors." (2009) Cancer Letters 282:137-145.*
"Abstracts from the 7th International Meeting of the Sphingolipid Club held in Leiden, The Netherlands, Nov. 14-16, 2008", Naunyn-Schmied Arch Pharmacol. 380(4):359-72 (2009).
Bidwell et al., "Development of elastin-like polypeptide for thermally targeted delivery of doxorubicin." Biochem Pharmacol. 73(5): 620-31 (2007).
Fuchs "EVI1and its role in myelodysplastic syndrome, myeloid leukemia and other malignant diseases." Casopis Lekaru Ceskych 145(8): 619-24 (2006).
Jazaeri et al., "Evaluation of EVI1 and EVI1s (Delta324) as potential therapeutic targets in ovarian cancer." Gynecol Oncol. 118(2): 189-95 (2010).
Kumar et al., "Evil Promotes Leukemogenesis by Anti-Apoptotic Rather Than Differentiation-Blocking Effects in Murine MLL-AF9 Leukemia." Abstract of Oral Presentation at 50th Annual American Society of Hematology Meeting Dec. 8, 2008, Blood 112(11): Abstract 593 (2008).
Liu et al., "Evi1 is a survival factor which conveys resistance to both TGFbeta- and taxol-mediated cell death via PI3K/AKT." Oncogene 25(25): 3565-75 (2006).
Liu et al., "A genetically synthetic protein-based cationic polymer for siRNA delivery." Med Hypotheses. 76(2): 239-40 (2011).
Mitani et al., "Growth inhibition of leukaemic cells carrying the t(3;21) by the AML1/EVI-1-specific antisense oligonucleotide." Br J Haematol. 90(3): 711-14 (1995).
Perkins et al., "Role of EVI1 in cell cycle regulation: Relevance of specific target genes." Abstract of Poster Presented at 47th Annual American Society of Hematology Meeting Dec. 10-13, 2005, Blood 106(11): Abstract 1614 (2005).
Wieser, "The oncogene and developmental regulator EVI1: expression, biochemical properties, and biological functions." Gene 396(2): 346-57 (2007).
International Search Report from International Application No. PCT/US2011/037609 mailed Aug. 5, 2011.
International Search Report from International Application No. PCT/US2011/058856 mailed Jun. 22, 2012.
Aina et al., "Near-Infrared Optical Imaging of Ovarian Cancer Xenografts with Novel alpha3-Integrin Binding Peptide "OA02"." Mol Imaging 4(4): 439-47 (2005).
Bae et al., "Intelligent biosynthetic nanobiomaterials for hyperthermic combination chemotherapy and thermal drug targeting of HSP90 inhibitor geldanamycin." J Controlled Release 122(1): 16-23 (2007).
Bedi et al., "Delivery of siRNA into breast cancer cells via phage fusion protein-targeted liposomes." Nanomedicine 7 (3): 315-23 (2011).
Brannon-Peppas & Blanchette, "Nanoparticle and targeted systems for cancer therapy." Adv Drug Deily Rev 56(11):1649-59 (2004).
Cappello et al., "In-situ self-assembling protein polymer gel systems for administration, delivery, and release of drugs." Journal of Controlled Release 53(1-3): 105-17 (1998).

(Continued)

*Primary Examiner* — Jean C. Witz
*Assistant Examiner* — Mindy Newman
(74) *Attorney, Agent, or Firm* — McDonnell Boehnen Hulbert & Berghoff LLP

(57) ABSTRACT

This invention describes a protein nanoparticle system for targeting siRNA or other drugs into tumors. The basis of the protein system is elastin-like peptides that self-assemble once exposed to the nucleic acid of the siRNA. Specific targeting peptides are fused to the core ELP structure by standard genetic engineering techniques. These targeting peptides confer specific binding of the nanoparticle to receptors on the surface of tumor cells and allow for uptake of the nanoparticle into the tumor cells.

19 Claims, 6 Drawing Sheets

(56) References Cited

OTHER PUBLICATIONS

Castanotto & Rossi, "The promises and pitfalls of RNA-interference-based therapeutics." Nature 457(7228): 426-33 (2009).
Cerqueira et al., "Overview of ribonucleotide reductase inhibitors: an appealing target in anti-tumour therapy." Curr Med Chem. 12(11): 1283-94 (2005).
Chen et al., "Intelligent biosynthetic nanobiomaterials (IBNs) for hyperthermic gene delivery." Pharm Res. 25(3): 683-91 (2007).
Chilkoti et al., "Design of thermally responsive, recombinant polypeptide carriers for targeted drug delivery." Adv Drug Deliv Rev 54(8): 1093-11 (2002).
DeRoock et al., "Synthetic peptides inhibit adhesion of human tumor cells to extracellular matrix proteins." Cancer Res. 61(8): 3308-13 (2001).
Dreher et al., "Temperature triggered self-assembly of polypeptides into multivalent spherical micelles." J Am Chem Soc 130(2): 687-94 (2008).
Du et al., "In vitro panning of a targeting peptide to hepatocarcinoma from a phage display peptide library." Biochem Biophys Res Commun. 342(3): 956-62 (2006).
Fire et al., "Potent and specific genetic interference by double-stranded RNA in *Caenorhabditis elegans*" Nature 391 (6669): 806-11 (1998).
Fogel et al., "L1 expression as a predictor of progression and survival in patients with uterine and ovarian carcinomas." Lancet 362(9387): 869-75 (2003).
Heidel et al., "Administration in non-human primates of escalating intravenous doses of targeted nanoparticles containing ribonucleotide reductase subunit M2 siRNA." Proc Natl Acad Sci USA 104(14): 5715-21 (2007).
Hibino et al., "Identification of an active site on the laminin alpha5 chain globular domain that binds to CD44 and inhibits malignancy." Cancer Res. 64(14): 4810-16 (2004).
Hoffman et al., "Progressive vascular changes in a transgenic mouse model of squamous cell carcinoma." Cancer Cell 4(5): 383-91 (2003).
Iwamoto et al., "YIGSR, a synthetic laminin pentapeptide, inhibits experimental metastasis formation." Science 238 (4830): 1132-34 (1987).
Joyce et al., "Stage specific vascular markers revealed by phage display in a mouse model of pancreatic islet tumorigenesis." Cancer Cell 4(5): 393-403 (2003).
Juhasz et al., "Analysis of ribonucleotide reductase M2 mRNA levels in patient samples after GTI-2040 antisense drug treatment." Oncol Rep.15(5): 1299-304 (2006).
Kelly & Jones, "Isolation of a colon tumor specific binding peptide using phage display selection." Neoplasia 5(5): 437-44 (2003).
Lee et al., "Targeting bladder tumor cells in vivo and in the urine with a peptide identified by phage display." Mol Cancer Res. 5(1): 11-19 (2007).
Liu et al., "Tumor accumulation, degradation and pharmacokinetics of elastin-like polypeptides in nude mice." J Control Release 116(2): 170-78 (2006).
Mackay et al., Self-assembling chimeric polypeptide-doxorubicin conjugate nanoparticles that abolish tumors after a single injection. Nature Mater. 8(12): 993-99 (2009).
McDaniel et al., "Drug delivery to solid tumors by elastin-like polypeptides." Adv. Drug Del Rev. 62(15): 1456-67 (2010).
Megeed et al., "Genetically engineered silk-elastin like protein polymers for controlled drug delivery." Advanced Drug Delivery Reviews 54(8): 1075-91 (2002).
Meyer & Chilkoti, "Purification of recombinant proteins by fusion with thermally responsive polypeptides." Nature Biotechnology 17: 1112-15 (1999).
Nanjundan et al., "Amplification of MDSJ/EVIJ and EVII, located in the 3q26.2 amplicon, is associated with favorable patient prognosis in ovarian cancer." Cancer Res. 67(7): 3074-84 (2007).
Newton et al., "In vivo selection of phage for the optical imaging of PC-3 human prostate carcinoma in mice." Neoplasia 8(9): 772-80 (2006).
Oyama et al., "Isolation of lung tumor specific peptides from a random peptide library: generation of diagnostic and cell targeting reagents." Cancer Lett. 202(2): 219-30 (2003).
Pierschbacher & Ruoslahti, "Cell attachment activity of fibronectin can be duplicated by small synthetic fragments of the molecule." Nature 309(5963): 30-33 (1984).
Romanov et al., "Phage display selection of peptides that affect prostate carcinoma cells attachment and invasion." Prostate 47(4): 239-51 (2001).
Shukla & Krag, "Selection of tumor-targeting agents on freshly excised human breast tumors using a phage display library." Oncol Rep. 13(4): 757-64 (2005).
Silletti et al., "Plasmin-sensitive dibasic sequences in the third fibronectin-like domain of L1-cell adhesion molecule (CAM) facilitate homomultimerization and concomitant integrin recruitment." J Cell Biol. 149(7): 1485-502 (2000).
Sroka et al., "The minimum element of a synthetic peptide required to block prostate tumor cell migration." Cancer Biol Ther. 5(11): 1556-62 (2006).
Urry et al., "Biocompatibility of the Bioelastic Materials, Poly(GVGVP) and Its Gamma-Irradiation Cross-Linked Matrix: Summary of Generic Biological Test Results." Journal of Bioactive and Compatible Polymers 6(3): 263-282 (1991).
Urry, "Physical Chemistry of Biological Free Energy Transduction As Demonstrated by Elastic Protein-Based Polymers." Journal of Physical Chemistry B 101(51): 11007-28 (1997).
Wright & Conticello, "Self-assembly of block copolymers derived from elastin mimetic polypeptide sequences." Advanced Drug Delivery Reviews 54(8):1057-73 (2004).
Yamaoka et al., "Mechanism for the phase transition of a genetically engineered elastin model peptide (VPGIG)(40) in aqueous solution." Biomacromolecules 4(6): 1680-85 (2003).
Zhang et al., "Neuroblastoma tumor cell-binding peptides identified through random peptide phage display." Cancer Lett. 171(2): 153-64 (2001).
Zhang et al., "Panning and identification of a colon tumor binding peptide from a phage display peptide library." J Biomol Screening 12(3): 429-35 (2007).
Zimmermann et al., "RNAi-mediated gene silencing in non-human primates." Nature 441(7089): 111-14 (2006).

\* cited by examiner

COMPOSITIONS OF A PEPTIDE TARGETING SYSTEM FOR TREATING CANCER

CROSS REFERENCE TO RELATED APPLICATION

This application claims benefit of U.S. Provisional Application No. 61/436,127, filed Nov. 1, 2010, which is incorporated herein by reference in its entirety.

BACKGROUND OF THE INVENTION

1. Field of the Invention

The invention generally concerns the fields of medicine and molecular biology. In particular, the invention concerns polypeptides for delivery of therapeutic molecules and methods for the use thereof.

2. Description of Related Art

Cancer, metabolic and infectious diseases, and other diseases are caused by the inappropriate activity of specific genes. The ability to silence genes selectively through RNA interference (RNAi) offers the potential to revolutionize the way diseases and illnesses are treated, by creating a new class of drugs aimed at eliminating specific gene-products or proteins from the cell. RNAi has been convincingly demonstrated in preclinical models of oncology, influenza, hepatitis, diabetes, macular degeneration, Parkinson's disease, Huntington's disease and many other areas of serious unmet medical need.

RNA interference, based upon the use of short interfering RNA (siRNA) duplexes, has many advantages for rapid development of an effective therapeutic agent. Based on the mRNA sequence for the target protein, siRNA therapeutics can be designed relatively quickly (compared to the time needed to synthesize and screen conventional small molecule drugs). Further, siRNA-based therapeutics can be designed to possess great specificity to the target mRNA of interest.

Several delivery vehicles that target siRNA to tumors are in clinical trials, yet have not been approved by the FDA (Castanotto and Rossi, 2009, *Nature* 457: 426-33; Zimmermann et al., 2006, *Nature* 441: 111-4). In these trials, systemic administration of siRNA with non-targeted nanoparticles could result in dose-dependent tumor accumulation and silencing of target gene expression (Juhasz et al., 2006, *Oncol Rep.* 15: 1299-304.). Despite these encouraging data, the genes targeted by these siRNAs are expressed in all normal cells, albeit at lower levels than in many tumor cells (Cerqueira et al., 2005, *Curr Med Chem.* 12: 1283-94; Heidel et al., 2007, *Proc Natl Acad Sci USA*. 104: 5715-21). A further common drawback to using non-targeting nanoparticles is their significant accumulation in the liver, kidney and spleen, leading to potential off-target effects and reducing effective doses of therapeutic payload to other organs.

RNA is rapidly degraded by RNA nucleases in the body, and siRNA drugs must be protected from these enzymes by encapsulating in a nanoparticle that can increase the concentration of the nucleotide in the circulating blood. The disadvantage of using siRNA is its rapid degradation by nucleases in the circulation. The primary challenge to the use of siRNAs as therapeutics in mammals is the intracellular delivery of intact siRNA to specific tissues and organs that express the target gene. Two important factors are essential for successful use of siRNA to treat disease: (1) selecting a specific genetic target responsible for promotion of the particular disease, and (2) a method of targeting the siRNA directly to the diseased cells. In cancer treatment, for example, selecting a specific oncogene as a siRNA target, and a method of targeting the siRNA directly to tumor cells.

However, these essential targeting factors have not yet been achieved. Thus there remains a need in the art for reagents and methods for targeted delivery of siRNA (and other drug molecules) to cells, particularly cancer cells, to improve their therapeutic effectiveness.

SUMMARY OF THE INVENTION

The instant invention overcomes deficiencies in the prior art by providing a polypeptide delivery vehicle for therapeutic compositions. Polypeptide delivery vehicles of the invention generally comprise an elastin-like polypeptide (ELP) in complex with a therapeutic molecule. For example, such an ELP composition may comprise an ELP complexed with a therapeutic small molecule, polypeptide or nucleic acid. In some cases, an ELP may be covalently linked to a therapeutic molecule. For instance, an ELP composition may comprise an ELP domain covalently linked to a small molecule or an ELP linked to a therapeutic polypeptide by a peptide bond (i.e., an ELP fusion protein). In some further cases, an ELP may be fused with a polypeptide that binds to a therapeutic molecule. Likewise, an ELP may be in complex with or covalently conjugated to a nucleic acid aptamer, such as an aptamer that binds to a therapeutic molecule.

The modular nature of the described nanoparticle system provides advantageous flexibility over current liposome or nanoparticle drug delivery systems in that different drug binding or cell targeting peptide sequences can readily be introduced into the structure of the molecule, either by chemical synthesis or recombinant DNA technology. In a non-limiting example, a nucleic acid encoding a polypeptide according to the invention can be cloned into the plasmid vector used to prepare the nanoparticle polypeptide, wherein particular targeting sequences can be introduced into particular embodiments thereof. Another advantage is simplicity of manufacturing, wherein recombinant vectors or expression constructs can be introduced into the appropriate cell type (e.g., a plasmid with the DNA sequence for the nanoparticle polypeptide introduced into bacterial cell), where the polypeptide is produced in high quantities, and purified using specific binding, inter alia, a DNA affinity column.

BRIEF DESCRIPTION OF THE DRAWINGS

Figure 3:
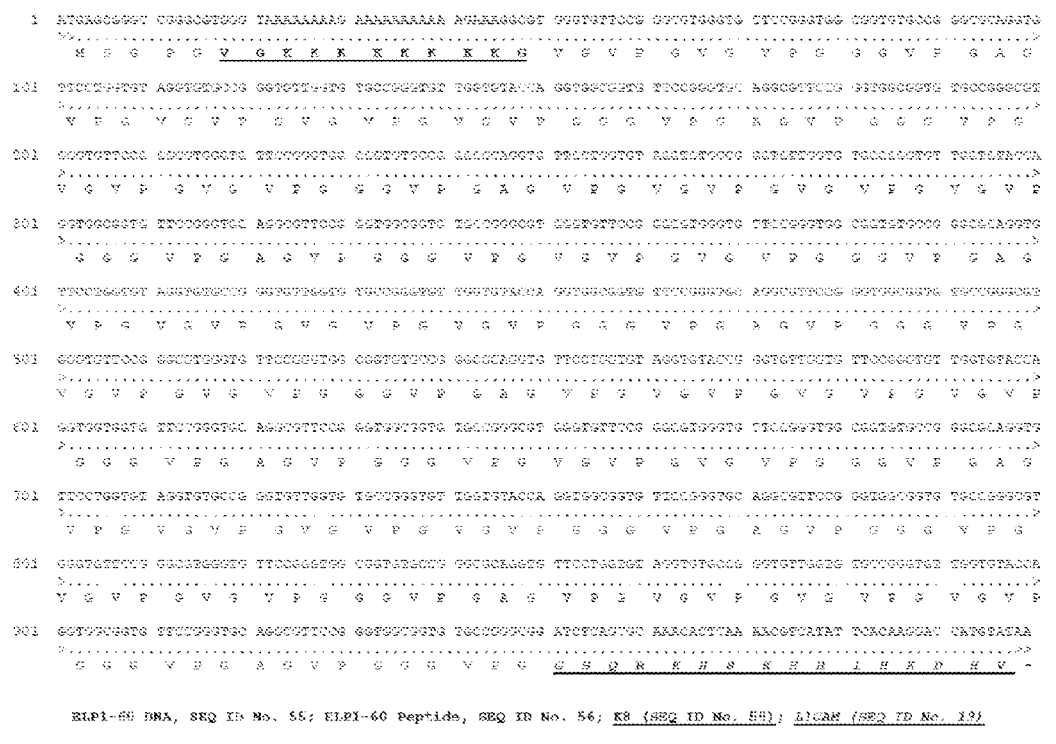

FIG. 3. Nucleotide and peptide sequence of sample particle. ELP1-60; K8 sequence (underline, bold); L1CAM sequence (underline, bold, italics)

DETAILED DESCRIPTION OF THE PREFERRED EMBODIMENTS

Figure 1:
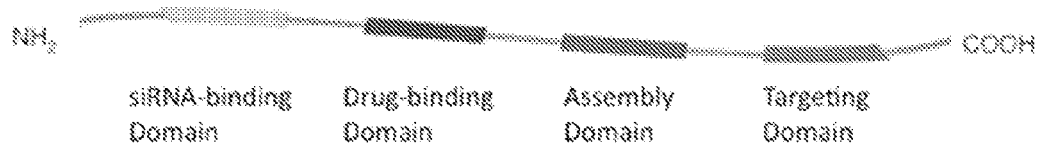
FIG. 1. Structure and domains of ELP drug delivery nanoparticles. ELP drug delivery systems as provided herein comprise an assembly domain (AD), a drug-binding domain (DBD), a nucleotide binding domain (NBD), and a cell targeting domain (CTD) that interacts with biological molecules of targeted cells.

Conventional techniques well known to those with skill in the art were used for oligonucleotide synthesis, or chemical polypeptide synthesis. Enzymatic reactions and purification techniques were performed according to manufacturers' specifications or as commonly accomplished in the art or as described herein. The techniques and procedures were generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., and Benoiton, N. L., Chemistry of Peptide Synthesis, 1$^{st}$ Ed, CRC Press (Aug. 12, 2005) which are incorporated herein by reference for any purpose. Unless specific definitions are provided, the nomenclature utilized in connection with, and the laboratory procedures and techniques of, molecular biology, genetic engineering, analytical chemistry, synthetic organic chemistry, and medicinal and pharmaceutical chemistry described herein are those well-known and commonly used in the art. Standard techniques can be used for chemical syntheses, chemical analyses, and treatment of patients.

Unless otherwise required by context, singular terms shall include pluralities and plural terms shall include the singular.

As utilized in accordance with the present disclosure, the following terms, unless otherwise indicated, shall be understood to have the following meanings.

1. Polypeptides

In one aspect, the invention describes an isolated polypeptide comprising a nucleic acid binding domain (NBD), an assembly domain (AD), and a cell targeting domain (CTD). In other embodiments, the isolated polypeptide further comprises a drug binding domain (DBD). In certain embodiments, the isolated polypeptide comprises the following segments: an AD, a CTD, a NBD, and a DBD. The domains of the polypeptides of the invention can be in any order, as readily apparent to one of ordinary skill in the art. The invention further describes a single polypeptide comprising multiple AD, CTD, NBD, and/or DBD domains.

In certain embodiments, the present invention concerns compositions comprising at least one polypeptide, such as elastin-like polypeptides. As used herein, a "polypeptide" generally refers, but is not limited to, a protein molecule containing at least one polypeptide with multiple amino acids. The protein may contain more than one polypeptide, such as a dimer or trimer or other tertiary structure. In some embodiments, a protein refers to a polypeptide that has 3 amino acids or more or to a peptide of from 3 to 100 amino acids. The terms "polypeptide" and "protein" are used interchangeably.

In certain embodiments the size of the polypeptide may comprise, or be at most or at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600 or greater amino molecule residues, and any range derivable therein. Moreover, it may contain such lengths of contiguous amino acids from a polypeptide provided herein, such as an elastin polymer.

The polypeptides of the invention may be made by any technique known to those of skill in the art, including the expression of proteins, polypeptides or peptides through standard molecular biological techniques, the isolation of polypeptides from natural sources, or the chemical synthesis of polypeptides. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (on the World Wide Web at ncbi.nlm.nih.gov/). The coding regions for these known genes may be amplified and/or expressed using the techniques disclosed herein or as would be known to those of ordinary skill in the art. Alternatively, various commercial preparations of proteins, polypeptides and peptides are known to those of skill in the art.

In certain embodiments a polypeptide may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In some embodiments, it may be desirable to purify a protein, for example, the polypeptides of the current invention. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide or polypeptide are filtration, ion-exchange chromatography, exclusion chromatography, polyacrylamide gel electrophoresis, affinity chromatography, or isoelectric focusing. A particularly efficient method of purifying peptides is fast protein liquid chromatography or even HPLC. In the case of ELP compositions protein purification may also be aided by the thermal transition properties of the ELP domain as described in U.S. Pat. No. 6,852,834.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

2. Polynucleotides and Gene Expression

The polypeptides of the invention can be produced by conventional molecular biology techniques. In one aspect, the invention describes an isolated polynucleotide having a nucleotide sequence that encodes a polypeptide comprising a drug binding domain (DBD), an assembly domain (AD), and a cell targeting domain (CTD).

As used herein, the term "isolated polynucleotide" means a polynucleotide of genomic, cDNA, or synthetic origin or a combination thereof, which by virtue of its source the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "polynucleotide" as used herein means a polymeric form of nucleotides that are at least 10 bases in length. In certain embodiments, the bases can be ribonucleotides or deoxyribonucleotides or a modified form of either type of nucleotide. The term includes single and double stranded forms of DNA or RNA.

The term "oligonucleotide" as used herein includes naturally occurring, and modified nucleotides linked together by naturally occurring, and/or non-naturally occurring oligonucleotide linkages. Oligonucleotides are a polynucleotide subset generally comprising no more than 200 nucleotides. In certain embodiments, oligonucleotides are 10 to 60 nucleotides in length. In certain embodiments, oligonucleotides are 12, 13, 14, 15, 16, 17, 18, 19, 20, 21, or 30 to 40 bases in length. Oligonucleotides can be single stranded, e.g. for use as antisense RNAs, or double-stranded, as small interfering RNAs (siRNAs) or small (or short) hairpin RNAs (shRNAs). An oligonucleotide can include a detectable label, such as a radiolabel, a fluorescent label, an antigenic label or a hapten.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotides linkages such as phosphate, phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res. 14: 9081; Stec et al., 1984, J. Am. Chem. Soc. 106: 6077; Stein et al., 1988, Nucl. Acids Res. 16: 3209; Zon et al., 1991, Anti-Cancer Drug Design 6: 539; Zon et al., 1991, OLIGONUCLEOTIDES AND ANALOGUES: A PRACTICAL APPROACH, (F. Eckstein, ed.), Oxford University Press, Oxford England, pp. 87-108; Stec et al., U.S. Pat. No. 5,151,510; Uhlmann and Peyman, 1990, Chemical Reviews 90: 543, the disclosures of each of which are hereby incorporated by reference for any purpose.

In another aspect, the invention describes a recombinant expression construct comprising a polynucleotide having a nucleotide sequence that encodes an assembly domain (AD), a cell targeting domain (CTD), and a drug binding domain (DBD).

The term "recombinant expression construct" is used to refer to a molecule (e.g., nucleic acid, plasmid, or virus) used to transfer coding information to a host cell or a target cell. The term "recombinant expression construct" and "vector" can be used interchangeably. Viral vectors suitable for the methods of the invention include those derived from, for example, adenovirus, adeno-associated virus, retroviruses, herpes simplex virus, or vaccinia virus.

The term "expression vector" refers to a vector that is suitable for transformation of a host cell or a target cell and contains nucleic acid sequences comprising control sequences that direct and/or control the expression of inserted nucleic acid sequences. The term "expression" includes, but is not limited to, processes such as transcription and RNA splicing, if introns are present.

An expression vector of the invention can comprise a DNA or RNA sequence having a coding sequence that is operatively linked to a control sequence. The term "control sequence" or "control element" as used herein refers to polynucleotide sequences that can affect the expression and processing of coding sequences to which they are ligated. The nature of such control sequences can differ depending upon the host organism. According to certain embodiments, control sequences for prokaryotes can include promoters, repressors, operators, ribosomal binding sites, and transcription termination sequences and antisense mRNA. According to certain embodiments, control sequences for eukaryotes can include promoters, enhancers and transcription termination sequences, or sequences that regulate protein degradation, mRNA degradation, nuclear localization, nuclear export, cytoplasmic retention, protein phosphorylation, protein acetylation, protein sumolation, or RNA inhibition (RNAi). In certain embodiments, "control sequences" can include leader sequences and/or fusion partner sequences. "Control sequences" are "operatively linked" to a coding sequence when the "control sequence" effects expression and processing of coding sequences to which they are ligated.

Typically, expression vectors used in a host cells or target cell contain sequences for vector maintenance and for expression of exogenous nucleotide sequences. Such sequences, collectively referred to as "flanking sequences" in certain embodiments will typically include one or more of the following nucleotide sequences: a promoter, one or more enhancer sequences, a transcriptional termination sequence, a complete intron sequence containing a donor and acceptor splice site, a ribosome binding site, a polyadenylation signal sequence, a polylinker region comprising one or a plurality of restriction endonuclease sites for inserting nucleic acid encoding an siRNA to be expressed, and a selectable marker element.

Flanking sequences can be homologous (i.e., from the same species and/or strain as the host cell or the target cell), heterologous (i.e., from a species other than the host cell or the target cell species or strain), hybrid (i.e., a combination of flanking sequences from more than one source), synthetic or native. As such, the source of a flanking sequence can be any prokaryotic or eukaryotic organism, any vertebrate or invertebrate organism, or any plant, provided that the flanking sequence is functional in, and can be activated by, the host cell or the target cell machinery.

Flanking sequences useful in the vectors of this invention can be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence can be known. The flanking sequence also can be synthesized using the methods described herein for nucleic acid synthesis or cloning.

Where all or only a portion of the flanking sequence is known, it can be obtained using in vitro amplification methods such as polymerase chain reaction (PCR) and/or by screening a genomic library with a suitable oligonucleotide and/or flanking sequence fragment from the same or another species. Where the flanking sequence is not known, a fragment of DNA containing a flanking sequence can be isolated from a larger piece of DNA that can contain, for example, a coding sequence or even another gene or genes. Isolation can be accomplished by restriction endonuclease digestion to produce the proper DNA fragment followed by isolation using agarose gel purification, Qiagen column chromatography (Chatsworth, Calif.), or other methods known to the skilled artisan. The selection of suitable enzymes to accomplish this purpose is readily apparent to one of ordinary skill in the art.

A transcription termination sequence is typically located 3' to the end of a polypeptide-coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein. Eukaryotes have a sequence that functions both as a transcription termination signal and as a poly A signal required for endonuclease cleavage followed by the addition of poly A residues (usually consisting of about 200 A residues).

The expression and cloning vectors of the present invention will typically contain a promoter that is recognized by the host organism and operatively linked to nucleic acid encoding a gene. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no experimental control over gene expression. A large number of promoters, recognized by a variety of potential host cells or target cells, are well known.

Suitable promoters for use with mammalian cells are well known and include, but are not limited to, those obtained from the genomes of eukaryotic viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region (Bernoist and Chambon, 1981, Nature 290: 304-10); the CMV promoter; the promoter contained in the 3' long terminal repeat of Rous sarcoma virus (Yamamoto, et al., 1980, Cell 22: 787-97); the herpes thymidine kinase promoter (Wagner et al., 1981, Proc. Natl. Acad. Sci. U.S.A. 78: 1444-45); and the regulatory sequences of the metallothionine gene (Brinster et al., 1982, Nature 296: 39-42). Also of interest are the following animal transcriptional control regions, which exhibit tissue specificity and have been utilized in transgenic animals: the elastase I gene control region that is active in pancreatic acinar cells (Swift et al., 1984, Cell 38: 639-46; Ornitz et al., 1986, Cold Spring Harbor Symp. Quaint. Biol. 50: 399409; MacDonald, 1987, Hepatology 7: 425-515); the insulin gene control region that is active in pancreatic beta cells (Hanahan, 1985, Nature 315: 115-22); the mouse mammary tumor virus control region that is active in testicular, breast, lymphoid and mast cells (Leder et al., 1986, Cell 45: 485-95); the beta-globin gene control region that is active in myeloid cells (Mogram et al., 1985, Nature 315: 338-40; Kollias et al., 1986, Cell 46: 89-94); the myelin basic protein gene control region that is active in oligodendrocyte cells in the brain (Readhead et al., 1987, Cell 48: 703-12); the myosin light chain-2 gene control region that is active in skeletal muscle (Sani, 1985, Nature 314: 283-86); the gonadotropic releasing hormone gene control region that is active in the hypothalamus (Mason et al., 1986, Science 234: 1372-78); and most particularly the immunoglobulin gene control region that is active in lymphoid cells (Grosschedl et al., 1984, Cell 38: 647-58; Adames et al., 1985, Nature 318: 533-38; Alexander et al., 1987, Mol. Cell Biol. 7: 1436-44).

Preferably, the promoter of an expression vector of the invention is active in the tissue from which a target or host cell is derived. For example, if the cell is a liver cell, one could advantageously use the albumin gene control region (Pinkert et al., 1987, Genes and Devel. 1: 268-76); the alpha-fetoprotein gene control region (Krumlauf et al., 1985, Mol. Cell Biol. 5: 1639-48; Hammer et al., 1987, Science 235: 53-58); or the alpha 1-antitrypsin gene control region (Kelsey et al., 1987, Genes and Devel. 1: 161-71), all of which are active in the liver.

The vectors of the invention can also contain an enhancer sequence that increases transcription in higher eukaryotic cells. Enhancers are cis-acting elements of DNA, are usually about 10-300 bp in length, and act on promoters to increase transcription. Enhancers are relatively orientation- and position-independent, They have been found within introns as well as within several kilobases both 5' and 3' to the transcription unit. Several enhancer sequences available from mammalian genes are known (e.g., enhancers from globin, elastase, albumin, alpha-feto-protein, insulin, transthyretin, and HNF-6 genes). An enhancer from a virus also can be used to increase expression of a gene. The SV40 enhancer, the cytomegalovirus early promoter enhancer, the polyoma enhancer, and adenovirus enhancers are exemplary enhancing elements for the activation of eukaryotic promoters. While an enhancer can be spliced into the vector at a position 5' or 3' to a nucleic acid molecule, it is typically located at a site 5' from the promoter.

Expression vectors of the invention can be constructed from a convenient starting vector such as a commercially available vector. Such vectors can or cannot contain all of the desired flanking sequences. Where one or more of the flanking sequences described herein are not already present in the vector, they can be individually obtained and ligated into the vector. Methods used for obtaining each of the flanking sequences are well known to one skilled in the art.

After the vector has been constructed and a nucleic acid molecule encoding, for example, the described ELP polypeptides, has been inserted into the proper site of the vector, the completed vector can be inserted into a suitable host cell or a target cell. The introduction of all expression vector encoding the described ELP polypeptides into a selected host cell or target cell can be accomplished by well-known methods including methods such as transfection, infection, calcium chloride, electroporation, microinjection, lipofection, DEAE-dextran method, or other known techniques as described above. The method selected will in part be a function of the type of host cell or target cell to be used. These methods and other suitable methods are well known to the skilled artisan, and are set forth, for example, in Sambrook et al., 2001, MOLECULAR CLONING: A LABORATORY MANUAL, 3d ed., Cold Spring Harbor Laboratory Press, Cold Spring Harbor, N.Y.

The term "transfection" is used to refer to the uptake of foreign or exogenous DNA by a cell, and a cell has been "transfected" when the exogenous DNA has been introduced inside the cell. A number of transfection techniques are well known in the art and are disclosed herein. See, e.g., Graham et al., 1973, Virology 52: 456; Sambrook et al., 2001, MOLECULAR CLONING: A LABORATORY MANUAL, 3d ed., Cold Spring Harbor Laboratory Press, Cold Spring Harbor, N.Y.; Davis et al., 1986, BASIC METHODS IN MOLECULAR BIOLOGY (Elsevier); and Chu et al., 1981, Gene 13: 197. Such techniques can be used to introduce an exogenous DNA into suitable host cells.

In other embodiments, the invention provides mammalian cells, for example, human cells, comprising an expression vector of the invention.

3. Assembly Domain (AD)

In certain embodiments, the AD is a protein-based polymer. In other embodiments, the AD comprises an elastin-like polypeptide (ELP).

As used herein the terms "elastin-like polypeptide" or "elastin-like repeat" (ELP) are used interchangeably. ELP refers to a class of amino acid polymers that undergo a conformation change dependent upon temperature. By increasing the temperature ELPs transition from elongated chains that are highly soluble into tightly folded assemblies with greatly reduced solubility (see U.S. Pat. No. 6,852,834). An ELP may, for example, be defined by the median temperature at which this phase transition occur. Thus, in certain aspects of the invention, an ELP will have a median phase transition temperature above about 37° C. In some further embodiments, an ELP may have a median phase transition temperature in a physiological range such as a transition temperature of about 38° C., 39° C., 40° C., 41° C., 42° C., 43° C., 44° C., 45° C. or 46° C. In some cases, ELPs may also be defined based upon the temperature range over which the phase transition occurs. For example, in some cases, the phase transition will occur over a temperature range of less than about 5° C. For instance phase transition may occur in a temperature range of about 4° C., 3° C., 2° C., 1° C. or less.

In some specific embodiments of the invention, an ELP domain may be defined by its amino acid sequence. For example, an ELP domain may comprise multiple repeats of the amino acid sequence VPGXG (SEQ ID No. 57), wherein X is any amino acid except proline. For example, an ELP of the invention may comprise 10 to 500 repeats of the VPGXG sequence. In some even more specific cases, an ELP of the invention may comprise between 50 and 300 or 80 and 200 amino acids. In some embodiments, the "X" residues in an ELP will all be the same amino acid, however certain other cases an ELP may comprise a variety different residues in the X position throughout the polymer. For example, in some cases X may be an alanine, a valine or a glycine residue, such as an ELP that comprises 10 VPGXG (SEQ ID No. 57) repeats wherein X=Val for the first five repeats, X=Ala for the next two repeats and X=Gly for the remaining 3 repeats (denoted $V_5:A_2:G_3$).

Protein-based polymers, such as ELPs, are a class of such polymers with favorable properties for a wide range of biomedical applications. ELPs are artificial peptide polymers composed of a (Val-Pro-Gly-X-Gly) (SEQ ID No. 57) repeat derived from human tropoelastin, wherein X, known as a "guest residue", can be any mixture of amino acids except proline. (Urry, D. W. Prog. Biophys. Mol. Biol. 57: 23-57, 1992.). The significance of ELPs as useful thermosensitive biomaterials was originally suggested by (D. T. McPherson, J. Xu, and D. W. Urry. Protein Expr. Purif. 7:51-57 (1996)).

ELPs are useful as ADs for multiple reasons. First, ELPs undergo an inverse phase transition in aqueous solutions at a characteristic transition temperature (Tt), above which they desolvate and phase separate from bulk water (Urry D. W., 1997, *Journal of Physical Chemistry B* 101:11007-11028.). For recombinant ELP block copolymers, this phase transition behavior promotes self-assembly into nanostructures, driven by selective desolvation of one block (Yamaoka et al., 2003, *Biomacromolecules* 4:1680-1685; Cappello et al., 1998, *Journal of Controlled Release* 53:105-117; Dreher et al., 2008, *J Am Chem Soc* 130:687-694). This can explain the ability of ELP to impart sufficient amphiphilicity to the polypeptide/drug mixture to drive its self-assembly into nanoparticles (Wright et al., 2002, *Advanced Drug Delivery Reviews* 54:1057-1073; Megeed et al., 2002, *Advanced Drug Delivery Reviews* 54:1075-1091). Second, ELPs are useful biopolymers, being non-toxic (Urry et al., 1991, *Journal of Bioactive and Compatible Polymers* 6:263-282; Liu et al., 2006, *J Control Release* 116:170-178), biodegradable, and displaying good pharmacokinetics (Chilkoti et al., 2002, *Adv Drug Deliv Rev* 54:1093-1111). Third, because ELPs can be produced via genetic engineering, their composition, molecular weight, and polydispersity can be precisely controlled. Fourth, ELPs can be produced with high yield (~100-200 mg/L) in *E. coli*, and can be easily and rapidly purified by exploiting their phase transition behavior (Meyer and Chilkoti, 1999, *Nature Biotechnology* 17:1112-1115) so that high-purity, clinical grade material is easily and cheaply obtained. The simplicity of construction brings consistency to nanoparticle manufacturing and siRNA formulation, a key concern for cGMP production and quality control. The utility and safety of ELPs has been demonstrated a Phase I clinical evaluation for treatment of diabetes (PhaseBio Pharmaceuticals, Inc.).

In further aspects of the invention, it is understood that the sequence of an ELP domain may be modified, for example, to change the phase transition characteristics of an ELP, ELP composition or nanoparticle. For instance, in some cases, an ELP domain comprises the sequence (Val-Pro-Gly-X-Gly) (SEQ ID No. 57), wherein X comprises any amino acid except proline. By substituting of different amino acids at the X position the characteristics of an ELP domain may be modified. For example, in the case where a lower transition temperature is desired more hydrophobic residues may be substituted at X. Conversely, to increase the transition temperature less hydrophobic residues may be substituted at the X position. The importance of hydrophobicity or the hydropathic amino acid index in conferring biologic function on a protein is generally understood in the art (Kyte & Doolittle, 1982, *J. Mol. Biol.* 157: 105-132). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). Thus, it will be understood that when the amino acid at position X has a high hydrophilicity value ELP transition temperature can be raised whereas to lower the transition temperature amino acids with lower hydrophilicity values may be used.

In certain embodiments, isolated polypeptides are designed and synthesized for gene delivery through recombinant DNA cloning technology based upon recursive directional ligation (RDL), a facile biosynthetic route achieved by conventional bacterial culture expression (14). In certain embodiments, the polypeptide comprises the amino acid sequence (Val-Pro-Gly-X-Gly)$_n$ (SEQ ID No. 57), wherein X is a peptide comprising Val, Ala and Gly; and n is an integer equal to or greater than 1. In other embodiments, n is 2, 5, 10, 20, 50, 100 or more. In more particular embodiments, X is a peptide comprising Val, Ala and Gly in a ratio of about 5:2:3. In particular embodiments, n is 60, noted as ELP(1-60). ELP (1-60) has been described in Chen et al. 2007, *Pharm. Res.* 25: 683-691, and is derived from ELP(1-30) as described in Meyer & Chilkoti, 1999, *Nat. Biotech.* 17, 1112-1115, which are each herein incorporated by reference in their entirety. Other block copolymers can be synthesized according to previous studies with recursive directional ligation.

It will also be understood that the transition temperature of an ELP domain, ELP composition or nanoparticle may be modified by changing the number of elastin-like repeats in an ELP domain. For example, in order to raise the transition temperature conferred by an ELP domain the number of ELP repeats may be reduced. Conversely, increasing the number of ELP repeats in an ELP domain will generally decrease the transition temperature of an ELP domain, ELP composition or nanoparticle.

In certain embodiments, a peptide or polypeptide may contain an amino acid sequence that is identical or similar to a reference sequence or a particular region of the reference sequence. In certain embodiments a peptide or polypeptide has at least or most 60, 65, 70, 75, 80, 85, 90, 95, 96, 97, 98, 99, 99.5, 100% identity with respect to the amino acid sequence of a particular polypeptide or within a region of the particular polypeptide. In some cases, an ELP domain sequence may modified to more closely match the sequence of a human elastin domain. Such modifications may be made, for example, to further reduce the immunogenicity of an ELP domain, or ELP composition (e.g., ELP fusion proteins). For example, in some embodiments of the invention, there an ELP domain may be defined as at least about 60, 65, 70, 75, 80, 85, 90 or 95% identical to the human elastin repeat sequence.

4. Cell Targeting Domain (CTD)

In particular and advantageous embodiments, polypeptides of the invention comprise one or more cell targeting domains (CTDs). Using conventional genetic engineering techniques, including recombinant DNA, nucleotide sequences for different cell-targeting domains can be included to determine their effects on the targeting of the polypeptide or nanoparticle.

The polypeptides of the invention can comprise a fusion protein comprising an AD and a CTD, and in further cases such a fusion protein can also comprise a NBD, and in further cases such a fusion protein can also comprise DBD.

In some embodiments of the invention, the polypeptide comprises a CTD that is an antibody or specific binding portion thereof, ligand, cytokine, chemokine or nucleic acid aptamer. "Specific binding portion" is defined as the peptide domain of the antibody that interacts with an antigen. Such a domain can be conjugated to an ELP composition of the invention. Cell targeting antibodies include, but are not limited to, polyclonal antibodies, monoclonal antibodies, single chain antibodies, antibody fragments, or humanized antibodies. In another example, a cell targeting ligand can be VEGF or the amino acids there from that mediate receptor binding. CTD can preferentially bind to certain classes of cells such as immune cells, cancer cells, or cells from a particular tissue or lineage. In certain aspects of the invention, CTD can also mediate internalization of an ELP-based composition.

In certain embodiments of the invention, the CTD can interact with biological molecules present on the surface of a target cell. In other embodiments, the CTD can interact with biological molecules present on the outer surface of a target cell. In other embodiments, the CTD can interact with biological molecules present on the inner surface of a target cell. In yet other embodiments, the CTD can interact with biological molecules present outside the cell. In yet other embodiments, the CTD can interact with biological molecules present inside the cell. The nanoparticle can condense such that the nanoparticle is permeable to the cell membrane. In such alternative embodiments, the nanoparticle can contact the biological molecule inside of the cell.

In other embodiments, the biological molecule comprises a receptor molecule. In certain embodiments, the biological molecule comprises a cell adhesion molecule. In other specific embodiments, the biological molecule comprises fibronectin or laminin. In certain embodiments, the biological molecule is present on the outer surface of the target cell, meaning that any part of the biological molecule is exposed to the outside of the cell, either in total or in part. In a particular embodiment, the invention describes a polypeptide comprising a CTD that binds tumor biomarkers on the surface of cancer cells.

The CTD is not limited to any particular polypeptide sequence. It can be designed to target any desired biological molecule. In specific particular embodiments, the biological molecule is specifically expressed in a desired cell type. As a non-limiting example, CTDs were designed to target biological molecules that are expressed in tumor cells but are not expressed in non-tumor cells. In certain embodiments, the CTD of the polypeptide comprises peptide ligands specific for tumor cells. Non-limiting examples of tumor specific CTD polypeptide sequences are shown in Table 1. In one embodiment, the CTD comprises a peptide ligand that binds the L1 cell adhesion molecule (L1CAM). Targeting specific tumor cells is advantageous due to the reduction of side-effects of cancer therapy by specific targeting of the drugs delivered in tumor-seeking ELP nanoparticles. The specific targeting can maintain or enhance the efficacy of cancer therapy while using lesser concentrations of drug agents. In one embodiment, the CTD comprises the peptide sequence (GSQRKHSKRHIHKDHV) (SEQ ID. No. 19).

TABLE 1

Tumor-Specific Peptide Ligands

| SEQ ID No. | Cancer | Peptide |
|---|---|---|
| SEQ ID No. 1 | Bladder | CSNRDARRC |
| SEQ ID No. 2 | Breast | VSQTMRQTAVPLLWFWTGSL |
| SEQ ID No. 3 | Breast | MTVCNASQRQAHAQATAVSL |
| SEQ ID No. 4 | Breast | RGDLATLRQLAQEDGVVGVR |
| SEQ ID No. 5 | Breast | DMPGTVLP |
| SEQ ID No. 6 | Laminin a5 | RLVSYNGIIFFLK |
| SEQ ID No. 7 | Colon | VHLGYAT |
| SEQ ID No. 8 | Colon | CPIEDRPMC |
| SEQ ID No. 9 | Fibronectin | RGD |
| SEQ ID No. 10 | Liver | TACHQHVRMVRP |
| SEQ ID No. 11 | Laminin b1 | YIGSRA |
| SEQ ID No. 12 | Lung | VSQTMRQTAVPLLWFWTGSL |
| SEQ ID No. 13 | Lung | MTVCNASQRQAHAQATAVSL |
| SEQ ID No. 14 | Lung | RGDLATLRQLAQEDGVVGVR |
| SEQ ID No. 15 | Lung | CGKRK |
| SEQ ID No. 16 | Lung | CDTRL |
| SEQ ID No. 17 | Lung | NGXGXX |
| SEQ ID No. 18 | Neuroblastoma | VPWMEPAYQRFL |
| SEQ ID No. 19 | Ovarian | GSQRKHSKRHIHKDHV |
| SEQ ID No. 20 | Ovarian | DGXGXX |
| SEQ ID No. 21 | Pancreas | KAA |
| SEQ ID No. 22 | Prostate | DPRATPGS |
| SEQ ID No. 23 | Prostate | IAGLATPGWSHWLAL |
| SEQ ID No. 24 | Prostate | DNRIRLQAKXX |

TABLE 1-continued

Tumor-Specific Peptide Ligands

| SEQ ID No. | Cancer | Peptide |
|---|---|---|
| SEQ ID No. 25 | Prostate | LNNIVSVNGRHX |
| SEQ ID No. 26 | Prostate | KIKMVISWKG |
| SEQ ID No. 27 | Skin | CSRPRRSEC |

In another aspect of the invention, methods are provided for targeting a drug agent to a target cell, which comprises using one or more polypeptides comprising an assembly domain (AD), a drug binding domain (DBD), and a cell targeting domain (CTD); contacting the drug agent with the DBD of one or more polypeptides; assembling the AD of one or more polypeptides to generate an assembled polypeptide; contacting the assembled polypeptide with the target cell; and contacting the CTD of the assembled polypeptide with a biological molecule present outside of the target cell. The term "obtaining" means taking physical possession of the physiological specimen. The manner in which the material is acquired is not limited to any specific process. In certain embodiments, the assembled polypeptide comprises a drug agent. In other embodiments, the assembled polypeptide can condense and form a nanoparticle. In other embodiments, the assembled polypeptide can condense with the drug agent and form a nanoparticle.

In certain embodiments, the methods of the invention target the drug agent to a desired cell. Any cell can be selected for targeting. In certain embodiments, the target cell is a eukaryotic cell, more preferably a mammalian cell and most preferably a rodent or human cell. In particular embodiments, the target cell is a tumor cell. Non-limiting examples of a tumor cell contemplated by the current invention include tumor cell is a human bladder cell, a human breast cell, a human colon cell, a human liver cell, a human lung cell, a human neuroblastoma cell, a human ovarian cell, a human pancreatic cell, a human prostate cell, or a human skin cell. In addition, a target cell can be selected based on the disease or condition that affects a patient who is to be treated by methods of the invention.

5. Drug Binding Domain (DBD)

In certain aspects of the invention, the polypeptide comprises a drug binding domain (DBD). The DBD can comprise any polypeptide sequence that binds a drug agent. The term "agent" or "drug agent" is used herein to denote a chemical compound, a mixture of chemical compounds, a biological macromolecule, or an extract made from biological materials. Drug agents include alkylating agents, antimetabolites, anthracyclines, plant alkaloids, topoisomerase inhibitors, and other antitumour agents. Other drug agents include Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea requires categorization, Idarubicin, Imatinib, Mechlorethamine, Mercaptopurine, Methotrexate, Mitoxantrone, Oxaliplatin, Paclitaxel, Pemetrexed, Teniposide, Tioguanine, Valrubicin, Vinblastine, Vincristine, Vindesine, and Vinorelbine.

In certain embodiments, the DBD can bind a conventional or investigational drug. In other embodiments, the DBD can bind an anti-neoplastic drug. In other embodiments, the polypeptide comprises multiple DBDs.

In certain embodiments, the DBD binds a therapeutic agent. In some embodiments, the therapeutic agent is a biologically active protein. Suitable proteins include those of interest in medicine, agriculture and other scientific and industrial fields, particularly including therapeutic proteins such as erythropoietins, inteferons, insulin, monoclonial antibodies, blood factors, colony stimulating factors, growth hormones, interleukins, growth factors, therapeutic vaccines, calcitonins, tumor necrosis factors (TNF), and enzymes. Specific examples of such therapeutic proteins include, without limitation, enzymes utilized in replacement therapy; hormones for promoting growth in animals, or cell growth in cell culture; and active proteinaceous substances used in various applications, e.g., in biotechnology or in medical diagnostics. Specific examples include, but are not limited to: superoxide dismutase, interferon, asparaginase, glutamase, arginase, arginine deaminase, adenosine deaminase ribonuclease, trypsin, chromotrypsin, papin, insulin, calcitonin, ACTH, glucagon, somatosin, somatropin, somatomedin, parathyroid hormone, erthyropoietin, hypothalamic releasing factors, prolactin, thyroid stimulating hormones, endorphins, enkephalins, and vasopressin. In other embodiments of the invention, the DBD comprises a therapeutic polypeptide domain. In certain aspects of the invention, the DBD can be chemically conjugated to an ELP domain, however in certain cases the ELP and therapeutic polypeptide domains can be comprised in a fusion protein. Therapeutic polypeptides for use the instant invention include, but are not limited to, cytokines, chemokines, angiogenic factors, anti-angiogenic factors. In some specific examples, a therapeutic polypeptide can be interferon (IFN), tumor necrosis factor (TNF), HIF-1, vascular endothelial growth factor (VEGF), fibroblast growth factor (FGF), platelet derived growth factor (PDGF), NF-kB inhibiting sequences, consensus interferon sequences, interleukin (IL)-2, IL-12, IL-4, IL-8 or a single chain antibody sequence (scFv) such as a VEGF specific scFv. In certain aspects of the invention, a therapeutic polypeptide can comprise an extra cellular domain of a receptor protein, such as VEGF receptor (VEGFR)-1 (Flt-1), VEGFR-2 (Flk-1/KDR) or VEGFR-3.

In certain embodiments, the agent is a diagnostic or imaging agent. The invention enables precise targeting for imaging or therapy. The term "imaging agent" is meant a compound designed to target a particular physiology or pathophysiology in a mammal, and which can be detected following its administration in vivo or in vitro. A non-limiting example of an imaging agent is a fluorescent label. Other labels are well known in the art.

In certain embodiments, the DBD comprises a nucleic acid binding moiety. In certain embodiments, the polypeptides of the invention comprise a DBD domain that comprises a cationic domain that binds nucleic acids. In particular embodiments, nucleic acid is a siRNA molecule. In other embodiments, the drug agent is a siRNA molecule.

6. Nucleic Acid Binding Domain (NBD)

In certain aspects of the invention, the polypeptide comprises a nucleic acid binding domain (NBD). In certain embodiments, the polypeptide comprises both a DBD and a NBD. In some embodiments, both the DBD and the NBD can bind nucleic acids. In particular embodiments, the NBD comprises a siRNA binding domain. In certain cases, the NBD can be conjugated to the ELP, for example via a covalent chemical conjugation. The NBD and the other domains of the polypeptide can be separated by spacer peptides. In some other cases, the polypeptide comprising the NBD can be a fusion protein comprising the NBD, AD and CTD.

Any nucleic acid binding polypeptide know in the art can be used for the NBD of the invention. For example, a NBD can bind to a specific nucleic acid sequence, such as the RNA binding domains of iron regulatory protein (IRP) 1 or 2. In certain additional cases, the NBD can bind to nucleic acids non-specifically, such as amino acid polymers that are rich in cationic residues. For example, a NBD can have of 25%, 30%, 35%, 40%, 45%, 50% or more residues that are positively charged at physiological pH, such as lysine. In certain instances, a NBD can comprise repeats of the amino acid sequence VK or VKG. For instance, the sequence can have 4 to 100 VK or VKG repeats or a mixture thereof, such as nucleic acid binding domain with 4, 8, 12, 16, 20, 24, 28, 32, 36, 40, 44, 48, 52, 56, 60, 64, 68, 72, 76, 80, 84, 88, 92, 96 or 100 VK or VKG repeats. Thus, a drug such as GA can be complexed with a NBD according to the present invention.

In certain embodiments, the NBD comprises an oligolysine domain, which comprises multiple lysine residues in sequential order. The oligolysine domain binds nucleic acids. In certain embodiments, the NBD comprises the amino acid sequence $(K)_n$, wherein n is an integer greater than 4. In a preferred embodiment, n is 8. (SEQ. ID. No. 58). In a particular embodiment, the NBD comprises the amino acid sequence $(K_8)$. (SEQ. ID. No. 58). In another preferred embodiment, the oligolysine domain comprises the amino acid sequence Lys-Lys-Lys-Lys-Lys-Lys-Lys-Lys-. (K8; SEQ. ID. No. 58).

In other embodiments, the NBD comprises an oligoarginine domain, which comprises multiple arginine residues in sequential order. In certain embodiments, the NBD comprises the amino acid sequence $(R)_n$, wherein n is an integer greater than 4. In particular embodiments, n=9 (R9; SEQ ID No. 59)

In particular embodiments, isolated polypeptides are composed of an oligolysine (K8) (SEQ. ID. No. 58) or oligoarginine (R9) (SEQ. ID. No. 59) and a ELP block with 60 repetitive pentapeptide units, represented as $(Val-Pro-Gly-X-Gly)_{60}$ or $(VPGXG)_{60}$, (Val-Pro-Gly-X-Gly =VPGXG =SEQ. ID. No. 57), wherein X is Val, Ala and Gly in a 5:2:3 ratio.

In particular embodiments, the drug agent comprises a siRNA molecule. In certain embodiments, the drug agent comprises a nucleotide with a sequence recognizing a portion of the RNA expressed from an oncogene.

In one embodiment of the invention, the drug agent comprises a nucleotide with a sequence recognizing a portion of the RNA expressed from the EVI1 gene Inhibition of the expression of EVI1 within a cell causes a block of the cell's division and/or an activation of apoptosis. In one embodiment of the invention, the nucleotide binds by Watson-Crick sequence complementarity to the EVI1 gene sequence to block its expression. The nucleotide can be a DNA oligonucleotide of a length sufficient to inhibit expression of the EVI1 gene at the DNA or RNA level. In another embodiment, the nucleotide can be double-stranded RNA (dsRNA) that, in association with the RNA processing mechanism, downregulates the expression of EVI1. This dsRNA can be a small interfering RNA (siRNA) of approximately 20 basepairs.

In certain embodiments, this application relates to double stranded RNAs (dsRNA) and RNAi constructs. The term "dsRNA" as used herein refers to a double stranded RNA molecule capable of RNA interference (RNAi), including siRNA. In addition, RNAi is a term initially applied to a phenomenon observed in plants and worms where double-stranded RNA (dsRNA) blocks gene expression in a specific and post-transcriptional manner. RNAi provides a useful method of inhibiting or reducing gene expression in vitro or in vivo.

The term "short interfering RNA," "siRNA," or "short interfering nucleic acid," as used herein, refers to any nucleic acid capable of mediating RNAi or gene silencing when processed appropriately by a cell. For example, the siRNA can be a double-stranded polynucleotide molecule comprising self-complementary sense and antisense regions, wherein the antisense region comprises complementarity to a target gene. The siRNA can be a single-stranded hairpin polynucleotide having self-complementary sense and antisense regions, wherein the antisense region comprises complementarity to a target gene. The siRNA can be a circular single-stranded polynucleotide having two or more loop structures and a stem comprising self-complementary sense and antisense regions, wherein the antisense region comprises complementarity to a target gene, and wherein the circular polynucleotide can be processed either in vivo or in vitro to generate an active siRNA capable of mediating RNAi. The siRNA can also comprise a single stranded polynucleotide having complementarity to a target gene, wherein the single stranded polynucleotide can further comprise a terminal phosphate group, such as a 5'-phosphate, or 5',3'-diphosphate. In certain embodiments, the siRNAs are non-enzymatic nucleic acids that bind to a target nucleic acid and alter the activity of the target nucleic acid. Binding and/or activity of the siRNA can be facilitated by interaction with one or more protein or protein complexes, such as the RNA Induced Silencing Complex (or RISC). In certain embodiments, the siRNAs comprise a sequence that is complementary to a target sequence along a single contiguous sequence of one strand of the siRNA molecule.

Optionally, the siRNAs of the application contain a nucleotide sequence that hybridizes under physiologic conditions (e.g., in a cellular environment) to the nucleotide sequence of at least a portion of the mRNA transcript for the gene to be inhibited (the "target" gene). The double-stranded RNA need only be sufficiently similar to natural RNA that it has the ability to mediate RNAi. Thus, the application has the advantage of being able to tolerate sequence variations that might be expected due to genetic mutation, strain polymorphism or evolutionary divergence. The number of tolerated nucleotide mismatches between the target sequence and the siRNA sequence is no more than 1 in 5 basepairs, or 1 in 10 basepairs, or 1 in 20 basepairs, or 1 in 50 basepairs. Mismatches in the center of the siRNA duplex are most critical and can essentially abolish cleavage of the target RNA. In contrast, nucleotides at the 3' end of the siRNA strand that is complementary to the target RNA do not significantly contribute to specificity of the target recognition. Sequence identity can be optimized by sequence comparison and alignment algorithms known in the art and calculating the percent difference between the nucleotide sequences by, for example, the Smith-Waterman algorithm as implemented in the BESTFIT software program using default parameters. Greater than 90%, 95%, 96%, 97%, 98%, or 99% sequence identity, or even 100% sequence identity, between the siRNA and the portion of the target gene is preferred. Alternatively, the duplex region of the RNA can be defined functionally as a nucleotide sequence that is capable of hybridizing with a portion of the target gene transcript under stringent conditions (e.g., 400 mM NaCl, 40 mM PIPES pH 6.4, 1 mM EDTA, 50° C. or 70° C. hybridization for 12-16 hours; followed by washing).

The double-stranded structure of dsRNA can be formed by a single self-complementary RNA strand, two complementary RNA strands, or a DNA strand and a complementary RNA strand. Optionally, RNA duplex formation can be initiated either inside or outside the cell. The RNA can be introduced in an amount that allows delivery of at least one copy per cell. Higher doses (e.g., at least 5, 10, 100, 500 or 1000 copies per cell) of double-stranded material can yield more effective inhibition, while lower doses can also be useful for specific applications. Inhibition is sequence-specific in that nucleotide sequences corresponding to the duplex region of the RNA are targeted for inhibition.

As described herein, the subject siRNAs comprise a duplex region about 19-30 nucleotides in length, about 21-27 nucleotides in length, about 21-25 nucleotides in length, or about 21-23 nucleotides in length. The siRNAs are understood to recruit nuclease complexes and guide the complexes to the target gene transcript by pairing to the specific sequences. As a result, the target gene transcript is degraded by the nucleases in the protein complex. In certain embodiments, the siRNA molecules comprise a 3' hydroxyl group. In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 27 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of the subject dsRNAs (e.g., siRNAs) can be carried out by chemical synthetic methods or by recombinant nucleic acid techniques. Endogenous RNA polymerase of the treated cell can mediate transcription in vivo, or cloned RNA polymerase can be used for transcription in vitro. As used herein, dsRNA or siRNA molecules of the application need not be limited to those molecules containing only RNA, but further encompasses chemically-modified nucleotides and non-nucleotides. For example, the dsRNAs can include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA can be modified to include at least one of a nitrogen or sulfur heteroatom. Modifications in RNA structure can be tailored to allow specific genetic inhibition while avoiding a general response to dsRNA. Likewise, bases can be modified to block the activity of adenosine deaminase. The dsRNAs can be produced enzymatically or by partial/total organic synthesis, any modified ribonucleotide can be introduced by in vitro enzymatic or organic synthesis. Methods of chemically modifying RNA molecules can be adapted for modifying dsRNAs. Merely to illustrate, the backbone of an dsRNA or siRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the application lack 2'-hydroxy(2'-OH) containing nucleotides. In certain embodiments, the siRNA molecules comprise a phosphorothioate sense strand. In certain embodiments, the siRNA molecules comprise a phosphodiester antisense strand.

In a specific embodiment, at least one strand of the siRNA molecules has a 3' overhang from about 1 to about 10 nucleotides in length, about 1 to 5 nucleotides in length, about 1 to 3 nucleotides in length, or about 2 to 4 nucleotides in length. In certain embodiments, an siRNA can comprise one strand having a 3' overhang and the other strand is blunt-ended at the 3' end (e.g., does not have a 3' overhang). In another embodiment, an siRNA can comprise a 3' overhang on both strands. The length of the overhangs can be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and can be beneficial in vivo.

In another specific embodiment, the subject dsRNA can also be in the form of a long double-stranded RNA. For example, the dsRNA is at least 25, 50, 100, 200, 300 or 400 bases. In some cases, the dsRNA is 400-800 bases in length. Optionally, the dsRNAs are digested intracellularly, e.g., to produce siRNA sequences in the cell. However, use of long double-stranded RNAs in vivo is not always practical, presumably because of deleterious effects that can be caused by the sequence-independent dsRNA response. In such embodiments, the use of local delivery systems and/or agents which reduce the effects of interferon or PKR are preferred.

In a further specific embodiment, the dsRNA or siRNA is in the form of a short hairpin structure (shRNA). The shRNAs can be synthesized exogenously or can be formed by transcribing from RNA polymerase III promoters in vivo. Preferably, such shRNAs are engineered in cells or in an animal to ensure continuous and stable suppression of a target gene. It is known in the art that siRNAs can be produced by processing a hairpin RNA in the cell.

In certain embodiments, drug agents as provided by the invention are species of short interfering RNA (siRNA). The term "short interfering RNA" or "siRNA" as used herein refers to a double stranded nucleic acid molecule capable of RNA interference or "RNAi", as disclosed, for example, in Bass, 2001, Nature 411: 428-429; Elbashir et al., 2001, Nature 411: 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., Intentional PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. As used herein, siRNA molecules need not be limited to those molecules containing only RNA, but can further encompass chemically modified nucleotides and non-nucleotides having RNAi capacity or activity.

RNA interference refers to the process of sequence-specific post-transcriptional gene silencing in animals mediated by short interfering RNAs (siRNA) (Fire et al., 1998, Nature 391:806). The presence of long dsRNAs in cells stimulates the activity of a ribonuclease III enzyme referred to as "dicer." Dicer is involved in processing of the long dsRNA into siRNA, which are short pieces of dsRNA (Berstein et al., 2001, Nature 409:363). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., 2001, Science 293:834). The RNAi response also features an endonuclease complex containing an siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex (Elbashir et al., 2001, Genes Dev. 15:188).

Short interfering RNA mediated RNAi has been studied in a variety of systems. Fire et al. were the first to observe RNAi in *C. elegans* (1998, Nature 391:806). Wianny and Goetz described RNAi mediated by dsRNA in mouse embryos (1999, Nature Cell Biol. 2:70). Hammond et al. described RNAi in *Drosophila* cells transfected with dsRNA (2000, Nature 404:293). Elbashir et al. described RNAi induced by introduction of duplexes of synthetic 21-nucleotide RNAs in cultured mammalian cells including human embryonic kidney and HeLa cells (2001, Nature 411:494).

Recent work in *Drosophila* embryo lysates has revealed certain requirements for siRNA length, structure, chemical composition, and sequence that are essential to mediate efficient RNAi activity. These studies have shown that siRNA duplexes comprising 21 nucleotides are most active when containing two nucleotide 3'-overhangs. Furthermore, substitution of one or both siRNA strands with 2'-deoxy or 2'-O-methyl nucleotides abolishes RNAi activity, whereas substitution of 3'-terminal siRNA nucleotides with deoxy nucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J. 20:6877). Other studies have indicated that a 5'-phosphate on the target-complementary strand of a siRNA duplex is required for siRNA activity and that ATP is utilized in cells to maintain the 5'-phosphate moiety on the siRNA (Nykanen et al., 2001, Cell 107:309). However siRNA molecules lacking a 5'-phosphate are active when introduced exogenously, suggesting that 5'-phosphorylation of siRNA constructs can occur in vivo.

A drug agent of the invention can be a double-stranded polynucleotide molecule comprising self-complementary sense and antisense regions, wherein the antisense region comprises a nucleotide sequence that is complementary to a portion of the nucleotide sequence and the sense region has a nucleotide sequence corresponding to the nucleic acid sequence or a portion thereof. The siRNA molecule can be assembled from two separate oligonucleotides, where one strand is the sense strand and the other is the antisense strand, wherein the antisense and sense strands are self-complementary. The siRNA molecule can also be assembled from a single oligonucleotide having self-complementary sense and antisense regions linked by means of a nucleic acid based or non-nucleic acid-based linker. The siRNA molecule can be a polynucleotide can form a substantially symmetrical duplex, asymmetric duplex, hairpin, or asymmetric hairpin secondary structure. The siRNA molecule can also comprise a single stranded polynucleotide having nucleotide sequence complementary to the nucleotide sequence or a portion thereof, wherein the single stranded polynucleotide can further comprise a terminal phosphate group, such as a 5',3'-diphosphate or a 5'-phosphate as discussed, for example, in Martinez et al., 2002, Cell 110:563-574 and Schwarz et al., 2002, Molecular: Cell 10:537-568.

In certain embodiments, siRNA molecules and other drug agents according to the invention can comprise a delivery vehicle, including liposomes and nanoparticles, for administration to a subject; carriers and diluents and their salts; and can be present in pharmaceutical compositions. In particular, siRNA is delivered in association with an ELP nanoparticle according to the invention. Methods for the delivery of nucleic acid molecules are described, for example, in Akhtar et al., 1992, Trends Cell Bio. 2:139; Delivery Strategies for Antisense Oligonucleotide Therapeutics, ed. Akhtar, 1995, Maurer et al., 1999, Mol. Membr. Biol. 16:129-140; Hofland and Huang, 1999, Handb. Exp. Pharmacol., 137:165-192; and Lee et al., 2000, *ACS Symp. Ser.* 752:184-192, all of which are incorporated herein by reference. Beigelman et al., U.S. Pat. No. 6,395,713 and Sullivan et al., PCT WO 94/02595, further describe general methods for delivery of nucleic acid molecules into cells and tissues. These protocols can be utilized for the delivery of virtually any nucleic acid molecule into a cell. Nucleic acid molecules can be administered to cells by a variety of methods known to those of skill in the art, including, but not restricted to, encapsulation in liposomes, by iontophoresis, or by incorporation into other delivery vehicles, such as hydrogels, cyclodextrins, biodegradable nanocapsules, and bioadhesive microspheres, or by proteinaceous vectors (see, for example, O'Hare and Normand, International PCT Publication No. WO 00/53722).

Alternatively, the nucleic acid/vehicle combination can be locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res. 5:2330-2337 and Barry et al., International PCT Publication No. WO 99/31262. Many examples in the art describe delivery methods of oligonucleotides by osmotic pump, (see Chun et al., 1998, Neuroscience Letters 257:135-138, D'Aldin et al., 1998, Mol. Brain Research 55:151-164, Dryden et al., 1998, J. Endocrinol. 157:169-175, Ghirnikar et al., 1998, Neuroscience Letters 247:21-24) or direct infusion (Broaddus et al., 1997, Neurosurg. Focus 3, article 4). Other delivery routes include, but are not limited to oral delivery (such as in tablet or pill form) and/or intrathecal delivery (Gold, 1997, Neuroscience 76:1153-1158). More detailed descriptions of nucleic acid delivery and administration are provided in Sullivan et al., PCT WO 94/02595, Draper et al., PCT WO93/23569, Beigelman et al., PCT WO99/05094, and Klimuk et al., PCT WO99/04819, all of which are incorporated by reference herein.

Alternatively, the polypeptides of the invention can be expressed within cells from eukaryotic promoters (see for example, Izant and Weintraub, 1985, Science 229:345; McGarry and Lindquist, 1986, Proc. Natl. Acad. Sci USA 83:399; Scanlon et al., 1991, Proc. Natl. Acad. Sci. USA 88:10591-5; Kashani-Sabet et al., 1992, Antisense Res. Dev. 2:3-15; propulic et al., 1992, J. Virol. 66:1432-41; Weerasinghe et al., 1991, J. Virol. 65:5531-4; Ojwang et al., 1992, Proc. Natl. Acad. Sci. USA 89:10802-6; Chen et al., 1992, Nucleic Acids Res. 20:4581-9; Sarver et al., 1990, Science 247:1222-1225; Thompson et al., 1995, Nucleic Acids Res. 23:2259; Good et al., 1997, Gene Therapy 4: 45. Those skilled in the art will recognize that any nucleic acid can be expressed in eukaryotic cells using the appropriate DNA/RNA vector. The activity of such nucleic acids can be augmented by their release from the primary transcript by an enzymatic nucleic acid (Draper et al., PCT WO 93/23569, and Sullivan et al., PCT WO 94/02595; Ohkawa al., 1992, Nucleic Acids Symp. Ser. 27:15-6; Taira et al., 1991, Nucleic Acids Res. 19:5125-30; Ventura et al., 1993, Nucleic Acids Res. 21:3249-55; Chowrira et al., 1994, J. Biol. Chem. 269: 25856).

In another aspect of the invention, the polypeptides of the invention can be expressed from transcription units (see for example, Couture et al., 1996, TIG 12:510) inserted into DNA or RNA vectors. The recombinant vectors can be DNA plasmids or viral vectors. siRNA expressing viral vectors can be constructed based on, but not limited to, adeno-associated virus, retrovirus, adenovirus, or alphavirus. In another embodiment, pol III based constructs are used to express nucleic acid molecules of the invention (see for example, Thompson, U.S. Pat. Nos. 5,902,880 and 6,146,886). The recombinant vectors capable of expressing the siRNA molecules can be delivered as described above, and persist in target cells. Alternatively, viral vectors can be used that provide for transient expression of nucleic acid molecules. Such vectors can be repeatedly administered as necessary. Once expressed, the siRNA molecule interacts with the target mRNA and generates an RNAi response. Delivery of siRNA molecule expressing vectors can be systemic, such as by intravenous or intramuscular administration, by administration to target cells ex-planted from a subject followed by reintroduction into the subject, or by any other means that would allow for introduction into the desired target cell (for a review, see Couture et al., 1996, TIG. 12:510).

In other aspects, the invention provides expression vectors comprising: a) a transcription initiation region (e.g., eukaryotic pol I, II or III initiation region); b) a transcription termination region (e.g., eukaryotic pol I, II or III termination region); and c) a nucleic acid sequence encoding at least one of the siRNA molecules of the invention; wherein said sequence is operably linked to said initiation region and said termination region, in a manner that allows expression and/or delivery of the siRNA molecule. The vector can optionally include an open reading frame (ORF) for a protein operably linked on the 5' side or the 3'-side of the sequence encoding the siRNA of the invention; and/or an intron (intervening sequences).

Transcription of siRNA molecules can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA 87:6743-7; Gao and Huang 1993, Nucleic Acids Res. 21:2867-72; Lieber et al., 1993, Methods Enzymol. 217:47-66; Zhou et al., 1990, Mol Cell Biol. 10:4529-37). Several investigators have demonstrated that nucleic acid molecules expressed from such promoters can function in mammalian cells (e.g. Kashani-Sabet et al., 1992, Antisense Res. Dev. 2:3-15; Ojwang et al., 1992, Proc. Natl. Acad. Sci. USA 89:10802-6; Chen et al., 1992, Nucleic Acids Res. 20:4581-9; Yu et al., 1993, Proc. Natl. Acad. Sci. USA 90:6340-4; L'Huillier et al., 1992, EMBO J. 11:4411-8; Lisziewicz et al., 1993, Proc. Natl. Acad. Sci. U.S.A 90:8000-4; Thompson et al., 1995, Nucleic Acids Res. 23:2259; Sullenger and Cech, 1993, Science 262:1566). More specifically, transcription units such as the ones derived from genes encoding U6 small nuclear (snRNA), transfer RNA (tRNA) and adenovirus VA RNA are useful in generating high concentrations of desired RNA molecules such as siRNA in cells (Thompson et al., 1995, Nucleic Acids. Res. 23:2259; Couture et al., 1996, TIG 12:510, Noonberg et al., 1994, Nucleic Acid Res. 22:2830; Noonberg et al., U.S. Pat. No. 5,624,803; Good et al., 1997, Gene Ther. 4:45; Beigelman et al., International PCT Publication No. WO 96/18736. The above siRNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavilis vectors) (for a review see Couture et al., 1996, TIG 12:510).

Expression vectors that are useful in the practice of the invention include expression vectors that comprise a nucleic acid sequence encoding two complementary sequences of an siRNA molecule separated by a small nucleotide spacer sequence, in a manner that allows expression of that siRNA molecule containing a hairpin loop. Generally, a useful expression vector comprises: a) a transcription initiation region; b) a transcription termination region; and c) a nucleic acid sequence encoding two complementary sequences of an siRNA molecule separated by a small nucleotide spacer sequence; wherein the sequence is operably linked to the initiation region and the termination region, in a manner that allows expression and/or delivery of the siRNA molecule containing the small hairpin loop.

In certain embodiments, the invention provides pharmaceutical compositions comprising a therapeutically effective amount of a polypeptide, nanoparticle, or drug agent as provided herein together with a pharmaceutically acceptable diluent, carrier, solubilizer, emulsifier, preservative and/or adjuvant. The invention further provides pharmaceutical compositions comprising a polypeptide, nanoparticle, or drug agent as provided herein. In particular, siRNA and other drug agents are delivered in association with an ELP nanoparticle according to the invention.

Acceptable formulation materials preferably are nontoxic to recipients at the dosages and concentrations employed. The pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (Such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, 18.sup.th Edition, (A. R. Gennaro, ed.), 1990, Mack Publishing Company.

7. Nanoparticles

In another aspect, the invention describes a nanoparticle comprising one or more polypeptides comprising an assembly domain (AD) and a cell targeting domain (CTD), plus a nucleic acid-binding domain (NBD), and/or a drug binding domain (DBD). In certain embodiments, the nanoparticle further comprises a drug agent. In other embodiments, the nanoparticle further comprises a siRNA molecule.

Nanoparticles are typically chemically based shell structures that bind up a nucleotide or drug agent and stabilize the molecule in the blood. Nanoparticles often comprise sugar, dextran, calcium phosphate, chitosan, peptide and/or plastic polymers. Drug agent-loaded nanoparticles for cancer drug delivery preferably have the following properties: 1) be easy to synthesize in a few steps with high yield and purity; 2) assemble into monodisperse drug-loaded nanoparticles with a size below 100 nm; 3) allow encapsulation of diverse drugs; 4) exhibit favorable pharmacokinetics and tumor accumulation; 5) release the drug with controlled and tunable kinetics; 6) lead to a therapeutic response; and 7) degrade into non-toxic components to enable clearance from the body without adverse toxicity. Although a number of different nanoscale delivery systems have been proposed for cancer therapy, most do not satisfy these criteria, which are critical to move these systems into clinical practice.

In one embodiment, the invention describes the first example of polypeptide nanoparticles that assemble into near-monodisperse, sub-100 nm size nanoparticles upon drug attachment, and which are biodegradable and display good pharmacokinetics and tumor accumulation, low toxicity, and excellent in vivo efficacy in a murine tumor model by delivering siRNA to tumor cells using a targeted peptide. In particular embodiments, the polypeptides of the invention will form core-shell nanoparticles upon mixing with siRNA, oligo (lysine)/siRNA (core) and ELP/anti-receptor peptide (shell).

In particular embodiments, the polypeptides of the invention readily assemble in solution and form a nanoparticle. The term "assemble" is defined as to come together or collect in a mass such that a particle is formed. The solution can of any type. The solution can be aqueous. ELP polypeptides of the present invention undergo a reversible inverse temperature transition: they are structurally disordered and highly soluble in water below a transition temperature (Tt), but exhibit a sharp (2-3 degree) disorder-to-order phase transition when the temperature is raised above Tt, leading to desolvation and assembly of the polypeptides. The ELP assembles, when reaching sufficient size, can be readily removed and isolated from solution by centrifugation. Importantly, such phase transition is reversible, and the isolated ELP assembles can be completely resolubilized in buffer solution when the temperature is returned below the Tt of the ELPs.

Figure 2:
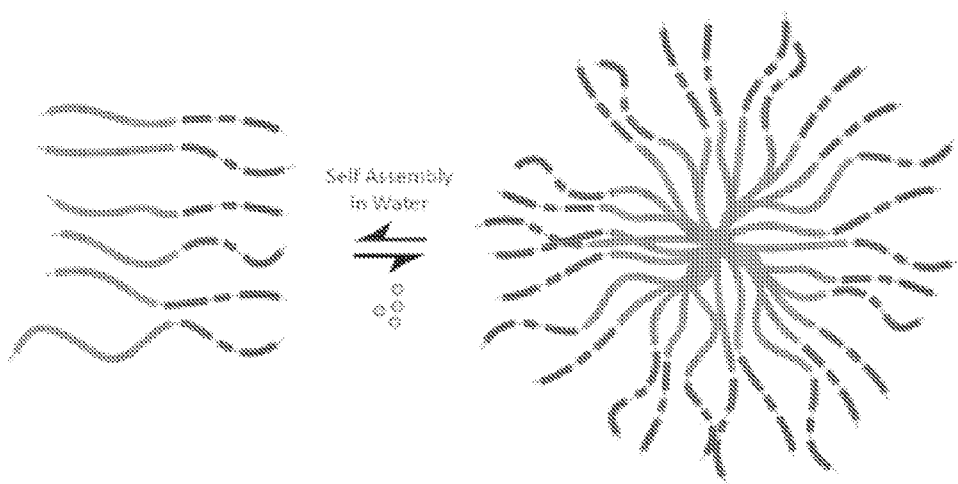
FIG. 2. Assembly of the ELP-nanoparticle in solution. The AD of each polypeptide causes the assembly into a large micelle.

Nanoparticles of the invention produced by assembly impel the subunits to organize into micelles of defined size, depending on the number of block repeats (~50-100 nm) (FIG. 2). The modular nature of the nanoparticle polypeptide provides the advantage of flexibility over current liposome or nanoparticle drug delivery systems in that different domain sequences, such as that containing a cell-targeting ligand, can readily be cloned into the plasmid vector used to prepare the ELP.

In certain embodiments, the nanoparticle comprises a single polypeptide. This can be a single polypeptide which interacts with its own ADs (intramolecular assembly). In other embodiments, the nanoparticle comprises a plurality of peptides. In this embodiment, the AD of a polypeptide interacts with the AD domain of a different polypeptide (intermolecular assembly). In other embodiments, the nanoparticle is chimeric.

In some further aspects of the invention, the nanoparticle comprises a therapeutic drug in complex with the polypeptide of the invention wherein the NBD is complexed with a nucleic acid. For example, a nanoparticle of the invention may comprise the polypeptide comprising a NBD complexed with a therapeutic nucleic acid. A nanoparticle of the invention may comprise a DNA or RNA molecule. For example, nucleic acids that may be used in a nanoparticle of the invention include, but are not limited to, DNA expression vectors, RNA expression vectors, siRNAs, miRNAs, aptamers and ribozymes. Nanoparticle nucleic acids may in some cases be therapeutic nucleic acids that may be used in gene therapy. For example, a therapeutic nucleic acid may induce apoptosis in cancer cells or restore the function a mutant gene to correct a genetic disorder. It will be understood by the skilled artisan that in some aspects of the invention a nanoparticle that comprises bound nucleic acid will release at least 20, 30 40, 50, 60, 70, 80, 90, 95 percent or more of the bound nucleic acid at temperatures above the transition temperature for the nanoparticle.

In still further embodiments, there is provided a method for making a nanoparticle comprising mixing the polypeptides of the invention with a nucleic acid molecule. In some cases, it will be understood that the soluble nanoparticle may be used to transfect cells with a nucleic acid. However, in certain aspects of the invention, a nanoparticle may be transitioned into an insoluble form in order to transfect a cell. A nanoparticle may be transitioned into an insoluble form (i.e., an aggregate) either before or after contacting a cell with the nanoparticle. In some specific cases, a nanoparticle maybe transitioned into an insoluble form by the application of heat (i.e., by increasing the temperature of the nanoparticle). Nanoparticle formulation is described generally in Merisko-Liversidge, et al., Toxicol Pathol (2008) 36: 43.

In certain embodiments, the nanoparticle is under 100 nm in size upon association with a drug agent. Packaging clinically approved drugs into nanoscale delivery vehicles (10-100 nm diameter) is of particular interest for cancer therapy, as numerous studies have shown that objects within this size range accumulate within solid tumors. This is thought to occur due to the enhanced permeability and retention (EPR) effect, which results from abnormalities of tumor blood and lymphatic vasculature.

The invention is not limited to ELP-nanoparticles. Other embodiments of the inventions can utilize liposomes, polydextran, or other polymers that (1) can carry a nucleotide molecule, (2) can or cannot carry a conventional chemotherapeutic agent, and (3) can accommodate a peptide molecule that targets specific tumor types or blocks tumor metastasis.

It is contemplated that a liposome composition may comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kanada et al., 1989, Science 243: 375-378). In another example, the lipid or liposome may be complexed or employed in conjunction with nuclear non-histone chromosomal proteins (HMG-1) (Kato et al., 1991, J. Biol. Chem., 266:3361-3364). In yet further embodiments, the lipid may be complexed or employed in conjunction with both HVJ and HMG-1.

In another embodiment of the invention, a drug agent is encapsulated in a liposome or nanoparticle that can protect the drug agent in the circulating blood and concentrate the drug agent in targeted tissues. In certain embodiments, the drug agent is a nucleotide. Liposomes are lipid surface molecules that form layers surrounding the nucleotide. Typically, cationic liposomes are used to encapsulate negatively charged nucleotides.

In a further embodiment of the invention, additional targeting ligands are associated with the liposome or nanoparticle containing the drug agent, that target receptors on tumor cells designated for apoptotic destruction. The liposomes can also be coated with polyethylene glycol (i.e., are PEGylated) to prolong the lifetime of the liposomes in the circulation. Similarly, nanoparticles can be so coated.

Targeting molecules can be organic chemical linkers termed aptamers that specifically bind receptors on the surface of a target cell. The aptamers can be covalently linked to the lipids of the liposome or polymers of the nanoparticles. Other molecules that can be used to target liposomes or nanoparticles to tumor cells are peptides, proteins or antibodies that are directed to a specific receptor on the surface of tumor cells.

Certain aspects of the invention concern methods for delivery of a drug to a cell by contacting the cell with the nanoparticle. It will be understood that such methods may comprise in vitro, ex vivo or in vivo nucleic acid delivery. Thus, in some cases, a nanoparticle of the invention may be administered to a human.

The term "pharmaceutical composition" as used herein refers to a composition comprising a pharmaceutically acceptable carrier, excipient, or diluent and a chemical compound, peptide, or composition as described herein that is capable of inducing a desired therapeutic effect when properly administered to a patient.

The term "therapeutically effective amount" refers to the amount of a pharmaceutical composition of the invention or a compound identified in a screening method of the invention determined to produce a therapeutic response in a mammal. Such therapeutically effective amounts are readily ascertained by one of ordinary skill in the art and using methods as described herein.

As used herein, "substantially pure" means an object species that is the predominant species present (i.e., on a molar basis it is more abundant than any other individual species in the composition). In certain embodiments, a substantially purified fraction is a composition wherein the object species comprises at least about 50 percent (on a molar basis or on a weight or number basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (wherein contaminating species cannot be detected in the composition by conventional detection methods) wherein the composition consists essentially of a single macromolecular species.

The term "patient" includes human and animal subjects.

Optimal pharmaceutical compositions can be determined by one skilled in the art depending upon, for example, the intended route of administration, delivery format and desired dosage. See, for example, REMINGTON'S PHARMACEUTICAL SCIENCES, Id. Such compositions can influence the physical state, stability, rate of in vivo release and rate of in vivo clearance of the invention.

Primary vehicles or carriers in a pharmaceutical composition can include, but are not limited to, water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which can further include sorbitol or a suitable substitute therefor. Pharmaceutical compositions of the invention can be prepared for storage by mixing the selected composition having the desired degree of purity with optional formulation agents (REMINGTON'S PHARMACEUTICAL SCIENCES, Id.) in the form of a lyophilized cake or an aqueous solution. Further, the nanoparticle can be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical compositions of the invention can be delivered parenterally. When parenteral administration is contemplated, the therapeutic compositions for use in this invention can be in the form of a pyrogen-free, parenterally acceptable aqueous solution comprising the desired nanoparticle of the invention. Preparation can involve the formulation of the desired molecule with an agent, such as injectable microspheres, bio-erodible particles, polymeric compounds (such as polylactic acid or polyglycolic acid), beads or liposomes, that can provide controlled or sustained release of the product which can then be delivered via a depot injection. Formulation with hyaluronic acid has the effect of promoting sustained duration in the circulation. Implantable drug delivery devices can be used to introduce the desired molecule.

The pharmaceutical compositions of the invention can be delivered through the digestive tract, such as orally. The preparation of such pharmaceutically acceptable compositions is within the skill of the art. A nanoparticle administered in this fashion can be formulated with or without those carriers customarily used in the compounding of solid dosage forms such as tablets and capsules. A capsule can be designed to release the active portion of the formulation at the point in the gastrointestinal tract when bioavailability is maximized and pre-systemic degradation is minimized. Additional agents can be included to facilitate absorption of the nanoparticle disclosed herein. Diluents, flavorings, low melting point waxes, vegetable oils, lubricants, suspending agents, tablet disintegrating agents, and binders can also be employed.

A pharmaceutical composition can involve an effective quantity of nanoparticle disclosed herein in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are evident to those skilled in the art, including formulations involving nanoparticles or compounds of the invention in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT Application No. PCT/US93/00829, which describes the controlled release of porous polymeric microparticles for the delivery of pharmaceutical compositions. Sustained-release preparations can include semipermeable polymer matrices in the form of shaped articles, e.g. films, or microcapsules, polyesters, hydrogels, polylactides (U.S. Pat. No. 3,773,919 and EP 058,481), copolymers of L-glutamic acid and gamma ethyl-L-glutamate (Sidman et al., 1983, Biopolymers 22: 547-556), poly(2-hydroxyethyl-methacrylate) (Langer et al., 1981, J. Biomed. Mater. Res. 15: 167-277) and Langer, 1982, Chem. Tech. 12: 98-105), ethylene vinyl acetate (Langer et al., id.) or poly-D(−)-3-hydroxybutyric acid (EP 133.988). Sustained release compositions can also include liposomes, which can be prepared by any of several methods known in the art. See e.g., Eppstein et al., 1985, Proc. Natl. Acad. Sci. USA 82: 3688-3692; EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

Once the pharmaceutical composition of the invention has been formulated, it can be stored in sterile vials as a solution, suspension, gel, emulsion, solid, or as a dehydrated or lyophilized powder. Such formulations can be stored either in a ready-to-use form or in a form (e.g., lyophilized) that is reconstituted prior to administration.

Pharmaceutical compositions of the invention can be administered alone or in combination with other therapeutic agents, in particular, in combination with other cancer therapy agents. Such agents generally include radiation therapy or chemotherapy. Chemotherapy, for example, can involve treatment with one or more of the following agents: anthracyclines, taxol, tamoxifene, doxorubicin, 5-fluorouracil, and other drugs known to one skilled in the art.

Introducing nanoparticles of the invention into cells can be accomplished using any method known in the art or as described herein. For example, local delivery of nanoparticles can be accomplished by direct injection. (Hefti, 1994, Neurobiology 25:1418-35.)

EXAMPLES

The following Examples illustrate certain aspects of the above-described method and advantageous results. The following examples are shown by way of illustration and not by way of limitation.

For the inventions described herein, examples are provided describing the formulation of siRNA into ELP-based nanoparticles containing a ligand for tumor-specific receptors. A series of assays to assess the physicochemical properties of these nanoparticles, both with and without siRNA loading, are performed to determine particle size and zeta potential (surface charge), siRNA incorporation efficiency, and serum stability. The fundamental nanoparticle described herein was engineered to have 60 pentameric repeats where the guest residues Xaa=Val:Ala:Gly [5:2:3]. This nanoparticle is a hydrophilic polymer (MW=24.5 kD) with a Tt=60° C. so that it exhibits high solubility at body temperature and has long plasma circulation as seen by its area under the concentration-time curve (AUC) (13). An oligolysine (K8; SEQ ID No. 58) or oligoarginine (R9; SEQ ID No. 59) segment is appended at the N-terminal end of the nanoparticle to provide siRNA attachment sites and impart sufficient amphiphilicity to the polymer. This segment provided eight or nine drug attachment points of lysine or arginine residues, respectfully, clustered at the N-terminal end of the nanoparticle.

Example 1

Preparation and Physicochemical and In Vitro Characterization of Receptor-targeted, ELP-Based Nanoparticles Loaded with siRNA in Cultured Human Cancer Cells The ability of siRNA to down-regulate its target gene at the mRNA (qPCR) and protein (Western blot) level is also examined in these cell lines. The ability of ELP-containing nanoparticles to be loaded with siRNA, protect it from nuclease degradation, facilitate uptake by ovarian cancer cells via receptor-mediated endocytosis, is confirmed by the following studies.

A small library of modular, cationic tri-block biopolymers with the following architecture: (i) oligo(lysine) for siRNA condensation; (ii) elastin-like polypeptide (ELP) block—(VPGXG)$_n$ (SEQ ID No. 57) with an X substitution ratio of $V_5:A_2:G_3$ for non-chromatographic purification and nanoparticle stability was genetically engineered for ovarian, breast, prostate, colon, lung and skin cancer cell targeting. This formed plasmid K8ELP(1-60)/pET25b. This recombinant approach provided precise control over biopolymer architecture and molecular weight with facile modular exchange and without the use of deleterious organic solvents compared to conventional synthetic polymers. The recombinant biopolymers formed core-shell nanoparticles upon mixing with siRNA, oligo(lysine)/siRNA (core) and ELP/anti-receptor peptide (shell).

Figure 4:
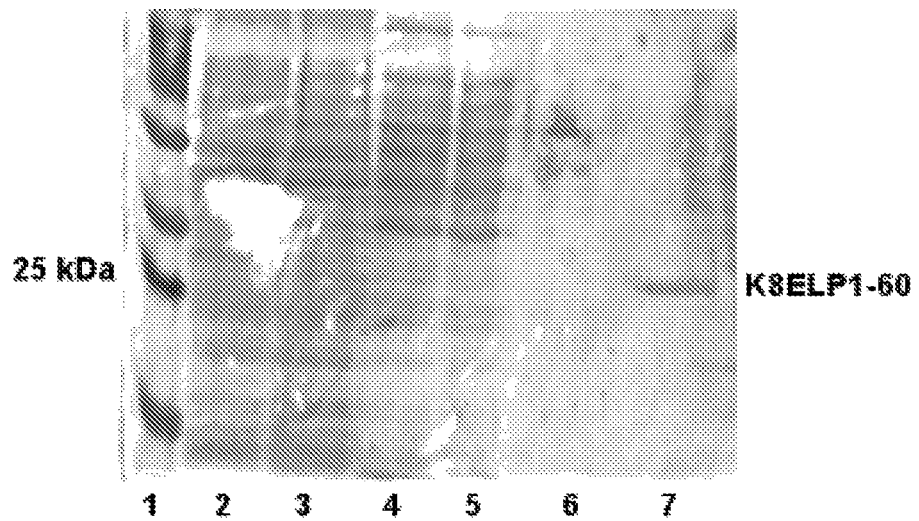
FIG. 4. Purification of K8ELP(1-60)-nanoparticle in water. SDS-PAGE analysis of purified fractions during inverse transition cycling procedure to isolate ELP-containing nanoparticle. Lane 1 STD, Lane 2 BLR, Lane 3 BLR+K8ELP1-60, Lane 4 Post Cell Disruption, Lane 5 Post PEI, Lane 6 Hot Spin Sup, Lane 7 Hot Spin pellet. The purified K8-ELP(1-60) is indicated at near 25 kDa size.

The anti-L1CAM sequence (GSQRKHSKRHIHKDHV) (SEQ ID No. 19), of the human L1CAM protein (NM_000425.3), was cloned at the XbaI/HindIII sites of K8ELP(1-60)/pET25b+ bacterial expression plasmids. Cloning in the proper orientation was confirmed by DNA sequencing. This formed the LK8ELP plasmid, and the peptide expressed was named LK8ELP. This expression plasmid was introduced into E. coli and grown overnight. Isopropyl β-D-1-thiogalactopyranoside (IPTG) (1 mM) was added to stimulate protein production. The ELP containing nanoparticles were purified through a non-chromatographic ITC technique that exploited the thermal-sensitivity of the ELP. The purity of the biopolymers was confirmed by SDS-PAGE analysis yielding a single protein band having an expected size of 25 kDa (see FIG. 4, lane 7).

Additional nucleotides expressing tumor-specific CTD peptides are also cloned into the K8ELP(1-60)/pET25b+ bacterial expression plasmids. The nucleotide sequences encoding these additional CTD peptides are shown in Table 5. Each of the resulting polypeptides are tested as described for LK8ELP.

Example 2

Nanoparticle Physicochemical Condensation Assays

Electrostatic condensation of siRNA to the purified K8ELP polypeptide was confirmed by gel retardation assays and Scatchard type analysis. siRNA is labeled at the 5' sense strand with DY547 (Dharmacon) or other suitable fluorescent label for cell-trafficking studies. The labeled siRNA was mixed at 0.2-2 N/P (molar ratio of cationic lysine amines from the biopolymer and anionic phosphate groups of the siRNA) and incubated at room temperature for 30 minutes in 1× tris base, acetic acid and EDTA (TAE), 5% glucose buffer. Biopolymer/siRNA nanoparticles were separated from free siRNA by Microcon-100 spin centrifugation. The concentrations of free and condensed siRNA were quantified by fluorometric spectrophotometry assay. The mixture was subjected to centrifugation through a Microcon-100 that retains the nanoparticle and bound siRNA, but allowed free siRNA to flow through. The concentrations of free and bound siRNA were determined using a fluorometric spectrophotometer and a standard curve of known concentrations of DY547 siRNA (Ex/Em 547/574). The affinity constant (KO of the biopolymer for siRNA was calculated by Scatchard plot analysis, with low micromolar ranges being obtained. This preparation is performed for all of the K8ELP polypeptides with the CTD.

Figure 5:
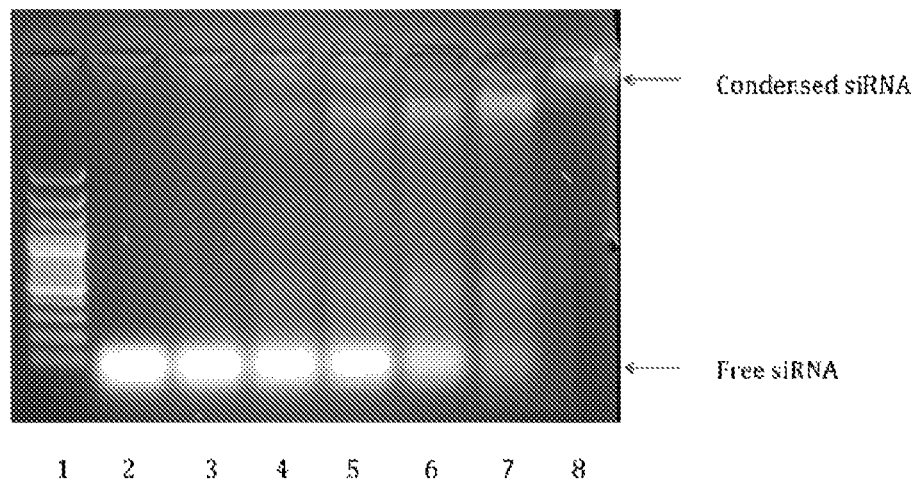
FIG. 5. Condensation of siRNA into K8ELP(1-60)-nanoparticle. Gel retardation analysis of siRNA bound to nanoparticle. siRNA (100 pmol) is mixed with serial dilutions of nanoparticle and incubated at ambient temperature for 30 min. The products are subjected to electrophoretic separation on a 1% agarose gel in 1×TAE buffer at 120V for 30 min. The gel contained ethidium bromide for visualization of siRNA. Lane 1 Ladder, Lane 2 siRNA (100 pmol), Lane 3 siRNA+1:320 K8ELP1-60, Lane 4 siRNA+1:160 K8ELP1-60, Lane 5 siRNA+1:80 K8ELP1-60, Lane 6 siRNA+1:40 K8ELP1-60, Lane 7 siRNA+1:20 K8ELP1-60, Lane 8 1:10 K8ELP1-60. Lane 8 has 1.33 ug of K8ELP(1-60).

Physicochemical characteristics of the K8ELP(1-60) nanoparticles were analyzed by gel retardation analysis of siRNA bound to nanoparticle. In this assay, siRNA (100 pmol) was mixed with serial dilutions of nanoparticle and incubated at ambient temperature for 30 min. The products are subjected to electrophoretic separation on a 1% agarose gel in 1×TAE buffer at 120V for 30 min. The gel contained ethidium bromide for visualization of siRNA. The siRNA condensed by K8ELP(1-60) nanoparticle does not leave the well (FIG. 5, lane 8). This gel retardation analysis is also performed for all of the K8ELP polypeptides with the CTD. Physicochemical characterization of the K8ELP(1-60) nanoparticle was also evaluated by dynamic light scattering and scanning electron microscopy, which showed a mean size of <100 nm with narrow distribution. Physicochemical characterization of all K8ELP) nanoparticles is also evaluated by zeta potential and RNase protection.

The stability of the nanoparticle in 100% human serum is also assessed by gel migration, SDS-PAGE, and fluorometric spectrophotometry for release of siRNA from the nanoparticle.

Example 3

Cell Targeting Domain Binding Assay

The ability of the L1CAM peptide of LK8ELP to bind tumor cells is examined via immunopreciptation assay. All other K8ELP peptides containing CTD are evaluated. Protein G MagnaBind Beads (Pierce, Rockford, Ill., Cat #21356) pre-coated with Protein G provided a ready-to-use means for purification of respective affinity targets. The high-affinity interaction between protein G and antibody does not disassociate efficiently except with very harsh conditions, such as boiling in sample loading buffer for SDS-PAGE or 8 M guanidine.HCl, pH 1.5. Magnetic beads are chosen over centrifugation or gravity methods to avoid any non-specific inclusion of nanoparticle in the precipitate.

Anti-receptor antibodies are prepared by standard polyclonal antibody production techniques in yellow goats (Bethyl Laboratories, Montgomery Tex.). Receptor-binding peptides are conjugated to keyhole limpet protein and injected repeatedly into goats. Anti-serum is isolated from goats after 8 weeks and antitumor cell binding is confirmed by Western blot analysis targeting protein isolated from tumor cells.

The ELP nanoparticle (0.75 mg per sample) is incubated overnight at 4° C. with and without 10 μg goat anti-human receptor antibody. Protein G MagnaBind Beads are added to a 96 deep-well plate (0.5 mg or 0.25 mg per well). Using a magnetic stand, the beads are washed with Tris-buffered saline containing 0.1% Tween-20, are incubated 1 hour with the nanoparticle sample/antibody mixture, washed three times and then eluted for 10 minutes at 96° C. with SDS-PAGE reducing sample buffer. Eluates are resolved by SDS-PAGE and analyzed by Western Blot with anti-receptor antibody.

Example 4

Localization of Nanoparticles to Tumors

The size and location of tumors are monitored non-invasively via whole-animal bioluminescence imaging (BLI). Two different nanoparticle formulations, one containing a ligand for a tumor-specific receptor (LK8ELP(1-60), the other lacking this peptide K8ELP(1-60), were prepared containing fluorescently (Dy677)-labeled siRNA. Groups (n=3) of tumor-bearing mice received a single intravenous injection of each nanoparticle formulation at one of three dose levels (1, 3, or 10 mg/kg with respect to siRNA). At three timepoints post-administration (0.5, 4, and 24 h), tumor localization of both K8ELP(1-60) nanoparticles was measured via whole-animal biofluorescence imaging.

Mice (20 g) were unilaterally injected in the left ovary intrabursally with 100,000 SKOV3ip2.luc-D3 metastatic human ovarian tumor cells. For the CTD peptides that target other cancers, the corresponding tumor cell lines are injected rather than ovarian tumor cells (see Table 2). The site of injection also will change based on the type of cancer tested (e.g. injection into lung, colon, brain). The presence of tumors was confirmed one-week post-injection by BLI imaging on the IVIS Spectrum. Fluorescent imaging was performed using the following excitation/emission filters and by auto exposure: EX: 605 nm; EM: 640, 660, 680, 700, 720, 740, 760, 780 nm; and EX: 675; EM: 720, 740, 760, 780 nm.

TABLE 2

Cancer Cell Lines

| Cancer Type | Cell Lines |
| --- | --- |
| Ovarian Cancer | A1847, OVCAR3, OVCAR5, and SKOV3 |
| Colon | HCT116, HT29 |
| Lung | SW900, H460, A549 |
| Bladder | HT1376, HT11197, RT4 |
| Breast | MDA-MB-231, MCF-7 |
| Neuroblastoma | SK-N-BE(1), SK-N-BE(2) |
| Prostate | LNCaP and PC3 |
| Melanoma | WM-266-4 |
| Pancreatic | HPAFII, PANC-1, PANC 03.27, or SW1990 |
| Liver | SK-HEP1, SNU-398 |

Figure 6:
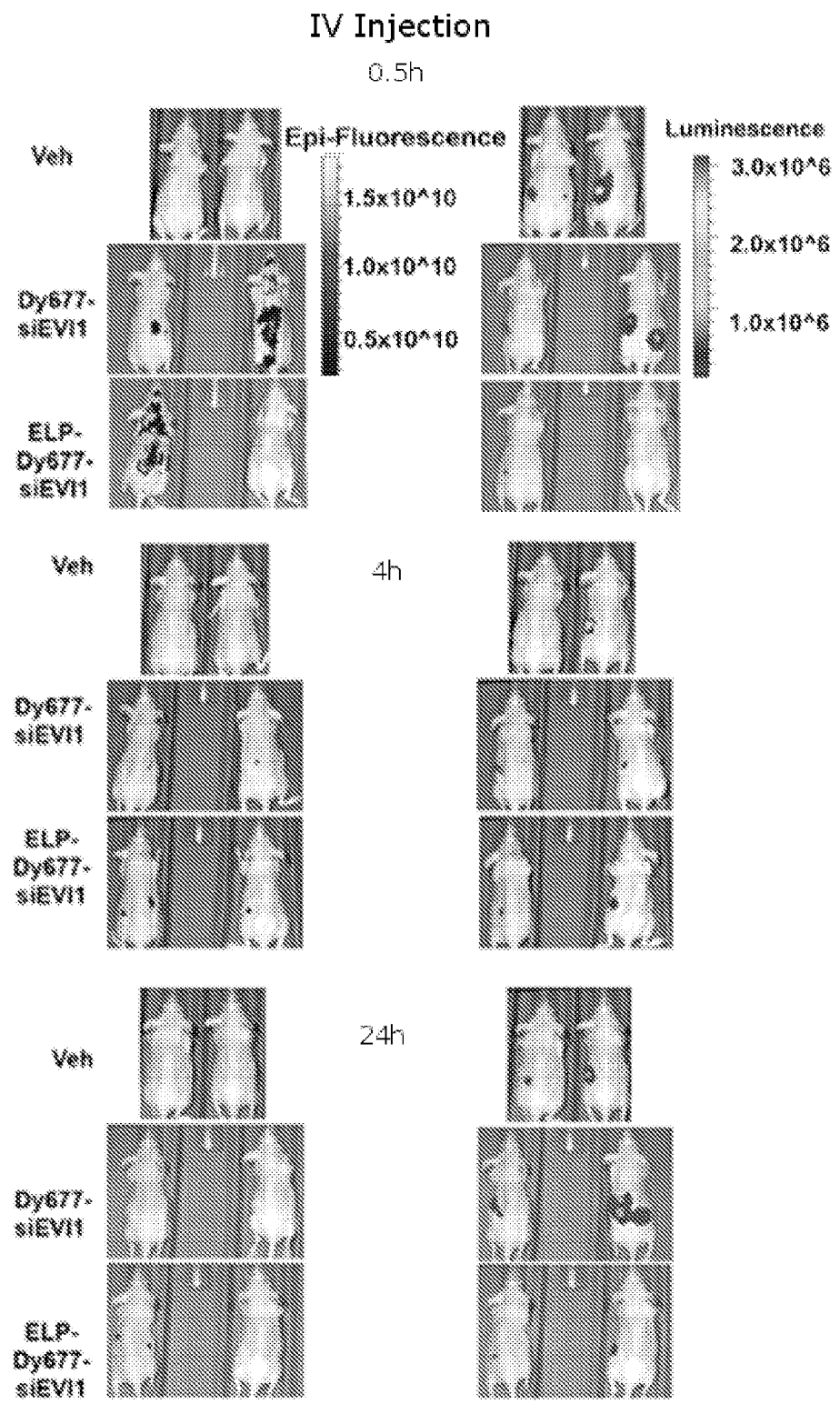
FIG. 6. Localization of nanoparticle containing labeled siRNA to tumors is performed by whole body bioluminescence imaging. Two mice each were injected with labeled naked siRNA (Dy677-siEVI1) as control and labeled siRNA in K8ELP(1-60) (Dy677-ELP-siEVI1) as treatment groups and are shown along with the vehicle group. Bioluminescent imaging is performed with exposure times that yield images that are not saturated. Spectral unmixing to lower background autofluorescence is performed using parameters for Cy5.5, which has very similar Ex/Em with Dy677. All fluorescent and BLI images for all time points (0.5, 4, and 24 h) are placed on the same scale so that a direct comparison can be made among time points. The fundamental K8ELP(1-60) nanoparticle containing labeled siRNA is found to specifically localize to tumors within 4 h, and is metabolized by the tumors so signal diminished by 24 h.

Two mice each were injected with labeled naked siRNA (Dy677-siEVI1) as control and labeled siRNA in K8ELP(1-60) (Dy677-ELP-siEVI1) as treatment groups and the results shown along with the vehicle group in FIG. 6. Bioluminescent imaging was performed with exposure times that yielded images that are not saturated. Spectral unmixing to lower background autofluorescence was performed using parameters for Cy5.5, which has very similar Ex/Em with Dy677. All fluorescent and BLI images for all time points (0.5, 4, and 24 h) were placed on the same scale so that a direct comparison can be made among time points. The fundamental K8ELP (1-60) nanoparticle containing labeled siRNA was found to specifically localize to tumors within 4 h, and was metabolized by the tumors so signal diminished by 24 h (See FIG. 6).

Example 5

Delivery of siRNA to Tumors

The ability of siRNA to down-regulate its target gene at the mRNA (qPCR) and protein (Western blot) level is also examined in a cancer cell line, according to Table 2. Confirmation of RNA interference is measured by 5' RACE techniques. The siRNA used for proof of principle was that of the oncogenic transcription factor EVI1. Tumors from mice are resected upon necropsy and stored in guanidinium isothiocyante TRI-Zol solution and frozen. Total RNA is isolated from mouse tumors using the TRIZol procedure (Invitrogen, Carlsbad, Calif.) according to manufacturer's instructions. PCR is performed following reverse transcription using random primers and AMV-reverse transcriptase.

Polymerase chain reaction (PCR) assays: PCR assays are performed to detect changes in EVI1 gene expression in the presence of the siRNA reagents described herein. For these assays, PCR reaction conditions used are a melting temperature of 95° for 60 sec; thermocycling at 95° C., for 30 sec, 60° C., for 30 sec, and 72° C., for 30 sec, for 25-30 cycles, and elongation 72° C. for 60 sec.

In these assays, total RNA is isolated from mouse tumor using TRIZol. Quantitative PCR (qPCR) was carried out using target-specific probes and primers obtained from Integrated DNA Technologies (Coralville, Iowa). Primers and reporters for EVI1 and β-actin mRNA are designed using the CloneManager program (Sci-Ed Software) and the sequences of forward and reverse primers are set forth below. PCR template cDNA was prepared using ThermoFisher Verso cDNA synthesis kit. All qPCR reagents are validated by demonstrating a linear relationship between sample concentration and amplification kinetics over a three-log range of nucleic acid concentrations, using cDNA made from total RNA. Taqman Universal Master Mix (Fermentas) is used for PCR reactions and amplification data is collected using an ABI Prism 7900 Sequence Detector and analyzed using Sequence Detection System software (SDS V2.0) from Applied Biosystems (Carlsbad, Calif.). Unless stated otherwise, mRNA abundance is calculated by normalization to β-actin $\Delta C_T = C_{Ttarget} - C_{T\beta-actin}$ and calibrated to mRNA abundance in untreated tumor cells ($\Delta\Delta CT = \Delta C_{TEVIRNA} \Delta C_{TsiGlo}$).

EVI1 mRNA abundance in cancer cells is normalized to β-actin and calibrated to HFC cells. Statistical analysis for QPCR results was carried out using the Mann-Whitney Rank Sum analytical function of Sigma Stat.

TABLE 3

EVI1 siRNA sequences

| Primer | Sequence (5' to 3') | Fragment Size |
| --- | --- | --- |
| EVI1 12-14 F | AAGGCATGTTCGCAACATCC (SEQ ID NO: 61) | 458 bp |
| EVI1 12-14 R | TAGTCATCCTCAGGGTTTCC (SEQ ID NO: 62) | 458 bp |
| β-actin F | GGGAAATCGTGCGTGACATTAAG (SEQ ID NO: 63) | 275 bp |
| β-actin R | TGTGTTGGCGTACAGGTCTTTG (SEQ ID NO: 64) | 275 bp |

5'-RLM-RACE: 5'-RLM-RACE is performed according to the Invitrogen GeneRacer manual with modifications. Two-to-eight micrograms of total RNA was ligated directly to 250 ng GeneRacer RNA adaptor:
(5'-CGACUGGAGCACGAGGACACUGACAUG-GACUGAAGGAGUAGAAA-3') (SEQ ID No. 64) using T4 RNA ligase (5 units) for 1 h at 37° C. After phenol extraction and ethanol precipitation, the purified ligation products were reverse-transcribed using SuperScriptIII (Invitrogen) and an EVI1 gene-specific reverse-transcription primer (5'-TAGT-CATCCTCAGGGTTTCC-3') (SEQ ID No. 61) at 55° C. for 45 min followed by inactivation at 70° C. 5'-RLM-RACE-PCR is performed using the GeneRacer 5' primer (5'-CGACTGGAGCACGAGGACACTGA-3') (SEQ ID No. 66) and an EVI1 gene-specific reverse primer (5'-TAGTCATCCTCAGGGTTTCC-3'). (SEQ ID No. 61). PCR is performed using a ABI Prism 7900 Sequence Detector and analyzed using the Sequence Detection System software (SDS V2.0) from ABI using PCR conditions of 95° C. for 3 min (1 cycle), 95° C. for 30 s, 60° C. for 30 s, 72° C. for 1 min (40 cycles), 72° C. for 10 min (1 cycle).

A second round of nested PCR is then performed using the GeneRacer 5' nested primer (5'-GGACACTGACATGGACTGAAGGAGTA-3') (SEQ ID No. 66) and an EVI1 gene-specific nested primer (5'-TAGTCATCCTCAGGGTTTCC-3') (SEQ ID No. 61). PCR products are run on a 2% agarose gel and stained with 1 μg μl$^{-1}$ ethidium bromide. PCR products are excised from the gel and sequenced directly to confirm RACE band identities. For the cell culture RACE experiments, 500,000 HT-144 melanoma cells are transfected with 20 nM EVI1 siRNA using Lipofectamine RNAiMax (Invitrogen). RNA is extracted for the RLM-RACE as described earlier, 48 h after transfection.

Western blot: Protein preparations from mouse tumor (80 ng/lane) are separated on 10% SDS-PAGE gels and immunoblots are developed by standard methods. OVCAR3 cell lines are used as positive controls for L1CAM immunoblots. Immunoblots are developed using goat anti-human receptor (1/50), rabbit anti-goat alkaline phosphatase (1/2000) coupled with the bischloroindolylphosphate/nitroblue tetrazolium substrate system. Densitometric areas for L1CAM are obtained using an Epson scanner at a resolution of 6000 d.p.i. and the data analyzed by MacBAS v2.0 quantitation software (Fuji Inc., Stamford, Conn.). Each peptide containing CTD is tested as described, using EVI1 as a test siRNA molecule.

All patents, patent applications, scientific article and other sources and references cited herein are explicitly incorporated by reference herein for the full extent of their teachings as if set forth in their entirety explicitly in this application.

It should be understood that the foregoing disclosure emphasizes certain specific embodiments of the invention and that all modifications or alternatives equivalent thereto are within the spirit and scope of the invention as set forth in the appended claims.

TABLE 4

Tumor-specific ligand nucleotide sequences

| PEPTIDE SEQ ID No. | Cancer | NUCLEOTIDE SEQ ID No. | Codon Sequence Optimized for Escherichia coli K12 |
|---|---|---|---|
| 1 | Bladder | 28 | TGCTCTAACCGTGACGCGCGTCGTTGC |
| 2 | Breast | 29 | GTTTCTCAGACCATGCGTCAGACCGCGGTTCCGCTGCTGTGGTTCTGGACCGGTTCTCTG |
| 3 | Breast | 30 | ATGACCGTTTGCAACGCGTCTCAGCGTCAGGCGCACGCGCAGGCGACCGCGGTTTCTCTG |
| 4 | Breast | 31 | CGTGGTGACCTGGCGACCCTGCGTCAGCTGGCGCAGGAAGACGGTGTTGTTGGTGTTCGT |
| 5 | Breast | 32 | GACATGCCGGGTACCGTTCTGCCG |
| 6 | Laminin a5 | 33 | CGTCTGGTTTCTTACAACGGTATCATCTTCTTCCTGAAA |
| 7 | Colon | 34 | GTTCACCTGGGTTACGCGACC |
| 8 | Colon | 35 | TGCCCGATCGAAGACCGTCCGATGTGC |
| 9 | Fibronectin | 36 | CGTGGTGAC |
| 10 | Liver | 37 | ACCGCGTGCCACCAGCACGTTCGTATGGTTCGTCCG |
| 11 | Laminin b1 | 38 | TACATCGGTTCTCGTGCG |
| 12 | Lung | 39 | GTTTCTCAGACCATGCGTCAGACCGCGGTTCCGCTGCTGTGGTTCTGGACCGGTTCTCTG |
| 13 | Lung | 40 | ATGACCGTTTGCAACGCGTCTCAGCGTCAGGCGCACGCGCAGGCGACCGCGGTTTCTCTG |
| 14 | Lung | 41 | CGTGGTGACCTGGCGACCCTGCGTCAGCTGGCGCAGGAAGACGGTGTTGTTGGTGTTCGT |
| 15 | Lung | 42 | TGCGGTAAACGTAAA |
| 16 | Lung | 43 | TGCGACACCCGTCTG |
| 17 | Lung | 44 | AACGGTnnnGGTnnnnnn |
| 18 | Neuroblastoma | 45 | GTTCCGTGGATGGAACCGGCGTACCAGCGTTTCCTG |
| 19 | Ovarian | 46 | GGTTCTCAGCGTAAACACTCTAAACGTCACATCCACAAAGACCACGTT |
| 20 | Ovarian | 47 | GACGGTnnnGGTnnnnnn |

TABLE 4-continued

Tumor-specific ligand nucleotide sequences

| PEPTIDE SEQ ID No. | Cancer | NUCLEOTIDE SEQ ID No. | Codon Sequence Optimized for *Escherichia coli* K12 |
|---|---|---|---|
| 21 | Pancreas | 48 | AAAGCGGCG |
| 22 | Prostate | 49 | GACCCGCGTGCGACCCCGGGTTCT |
| 23 | Prostate | 50 | ATCGCGGGTCTGGCGACCCCGGGTTGGTCTCACTGGCTGGCGCTG |
| 24 | Prostate | 51 | GACAACCGTATCCGTCTGCAGGCGAAAnnnnnn |
| 25 | Prostate | 52 | CTGAACAACATCGTTTCTGTTAACGGTCGTCACnnn |
| 26 | Prostate | 53 | AAAATCAAAATGGTTATCTCTTGGAAAGGT |
| 27 | Skin | 54 | TGCTCTCGTCCGCGTCGTTCTGAATGC |

TABLE 5

Other Sequences

| SEQ ID No. | Description | Sequence |
|---|---|---|
| 55 | LK8ELP nucleotide sequence | ATGAGCGGGC CGGGCGTGGG TAAAAAAAAG AAAAAAAAAA AGAAAGGCGT GGGTGTTCCG GCGCGTGGGTG TTCCGGGTGG CGGTGTGCCG GGCGCAGGTG TTCCTGGTGT AGGTGTGCCG GGTGTTGGTG TGCCGGGTGT TGGTGTACCA GGTGGCGGTG TTCCGGGTGC AGGCGTTCCG GGTGGCGGTG TGCCGGGCGT GGGTGTTCCG GGCGTGGGTG TTCCGGGTGG CGGTGTGCCG GGCGCAGGTG TTCCTGGTGT AGGTGTGCCG GGTGTTGGTG TGCCGGGTGT TGGTGTACCA GGTGGCGGTG TTCCGGGTGC AGGCGTTCCG GGTGGCGGTG TGCCGGGCGT GGGTGTTCCG GGCGTGGGTG TTCCGGGTGG CGGTGTGCCG GGCGCAGGTG TTCCTGGTGT AGGTGTACCG GGTGTTGGTG TTCCGGGTGT TGGTGTACCA GGTGGTGGTG TTCCGGGTGC AGGCGTTCCG GGTGGCGGTG TGCCGGGCGT GGGTGTTCCG GGCGTGGGTG TTCCGGGTGG CGGTGTGCCG GGCGCAGGTG TTCCTGGTGT AGGTGTGCCG GGTGTTGGTG TGCCGGGTGT TGGTGTACCA GGTGGCGGTG TTCCGGGTGC AGGCGTTCCG GGTGGCGGTG TGCCGGGCGT GGGTGTTCCG GGCGTGGGTG TTCCGGGTGG CGGTGTGCCG GGCGCAGGTG TTCCTGGTGT AGGTGTGCCG GGTGTTGGTG TGCCGGGTGT TGGTGTACCA GGTGGCGGTG TTCCGGGTGC AGGCGTTCCG GGTGGCGGTG TGCCGGGCGG ATCTCAGCGC AAACACTCAA AACGTCATAT TCACAAGGAC CATGTATAA |
| 56 | LK8ELP amino acid sequence | MSGPGVGKKKKKKKKGVGVPGVGVPGGGVPGAGVPGVGVPGVG VPGVGVPGGGVPGAGVPGGGVPGVGVPGVGVPGGGVPGAGVPGV GVPGVGVPGVGVPGGGVPGAGVPGGGVPGVGVPGVGVPGGGVPG AGVPGVGVPGVGVPGVGVPGGGVPGAGVPGGGVPGVGVPGVGVP GGGVPGAGVPGVGVPGVGVPGVGVPGGGVPGAGVPGGGVPGVGV PGVGVPGGGVPGAGVPGVGVPGVGVPGVGVPGGGVPGAGVPGGG VPGVGVPGVGVPGGGVPGAGVPGVGVPGVGVPGVGVPGGGVPGA GVPGGGVPGGSQRKHSKRHIHKDHV |
| 57 | ELP (X is Val, Ala and Gly in a 5:2:3 ratio) | VPGXG |
| 58 | K8 | VGKKKKKKKKG |
| 59 | K9 | VGRRRRRRRRRG |
| 60 | EVI1 12-14 F primer | AAGGCATGTTCGCAACATCC |
| 61 | EVI1 12-14 R primer | TAGTCATCCTCAGGGTTTCC |
| 62 | β-actin F primer | GGGAAATCGTGCGTGACATTAAG |
| 63 | β-actin R primer | TGTGTTGGCGTACAGGTCTTTG |

REFERENCES CITED

1. Fire, A., et al., *Potent and specific genetic interference by double-stranded RNA in Caenorhabditis elegans*. Nature, 1998. 391(6669): p. 806-11.
2. Brannon-Peppas L, Blanchette J O. Nanoparticle and targeted systems for cancer therapy. Adv Drug Deliv Rev 2004; 56:1649-1659.
3. Urry D W. Physical chemistry of biological free energy transduction as demonstrated by elastic protein-based polymers. Journal of Physical Chemistry B 1997; 101: 11007-11028.
4. Yamaoka T, et al. Mechanism for the phase transition of a genetically engineered elastin model peptide (VPGIG) (40) in aqueous solution. Biomacromolecules 2003; 4:1680-1685. [PubMed: 14606895]
5. Cappello J, et al. In-situ self-assembling protein polymer gel systems for administration, delivery, and release of drugs. Journal of Controlled Release 1998; 53:105-117. [PubMed: 9741918]
6. Dreher M R, et al. Temperature triggered self-assembly of polypeptides into multivalent spherical micelles. J Am Chem Soc 2008; 130:687-694. [PubMed: 18085778]
7. Wright E R, Conticello V P. Self-assembly of block copolymers derived from elastinmimetic polypeptide sequences. Advanced Drug Delivery Reviews 2002; 54:1057-1073. [PubMed: 12384307]
8. Megeed Z, Cappello J, Ghandehari H. Genetically engineered silk-elastinlike protein polymers for controlled drug delivery. Advanced Drug Delivery Reviews 2002; 54:1075-1091. [PubMed: 12384308]
9. Urry D W, Parker T M, Reid M C, Gowda D C. Biocompatibility of the Bioelastic Materials, Poly (Gvgvp) and Its Gamma-Irradiation Cross-Linked Matrix—Summary of Generic Biological Test-Results. Journal of Bioactive and Compatible Polymers 1991; 6:263-282.
10. Liu W, et al. Tumor accumulation, degradation and pharmacokinetics of elastin-like polypeptides in nude mice. J Control Release 2006; 116:170-178. [PubMed: 16919353]
11. Chilkoti A, Dreher M R, Meyer D E. Design of thermally responsive, recombinant polypeptide carriers for targeted drug delivery. Adv Drug Deliv Rev 2002; 54:1093-1111. [PubMed: 12384309]
12. Meyer D E, Chilkoti A. Purification of recombinant proteins by fusion with thermally-responsive polypeptides. Nature Biotechnology 1999; 17:1112-1115.
13. Liu W, et al. Tumor accumulation, degradation and pharmacokinetics of elastin-like polypeptides in nude mice. J Control Release 2006; 116:170-178.
14. McDaniel, J. R., Callahan, D. J., and Chilkoti, A. Drug delivery to solid tumors by elastin-like polypeptides. (2010) Adv. Drug Del Rev. 62: 1456-1467.
15. MacKay, J. A., Chen, M., McDaniel, J. R., Liu, W., Simnick, A. J., and Chilkoti, A. (2009) Self-assembling chimeric polypeptide-doxorubicin conjugate nanoparticles that abolish tumors after a single injection. Nature Mater. 8:993-999.
16. Castanotto, D. and J. J. Rossi, *The promises and pitfalls of RNA-interference-based therapeutics*. Nature, 2009. 457(7228): p. 426-33
17. Zimmermann, T. S., et al., *RNAi-mediated gene silencing in non-human primates*. Nature, 2006. 441(7089): p. 111-4.
18. Juhasz, A., et al., *Analysis of ribonucleotide reductase M2 mRNA levels in patient samples after GTI-2040 antisense drug treatment*. Oncol Rep, 2006. 15(5): p. 1299-304.
19. Cerqueira, N. M., et al., *Overview of ribonucleotide reductase inhibitors: an appealing target in anti-tumour therapy*. Curr Med Chem, 2005. 12(11): p. 1283-94.
20. Heidel, J. D., et al., *Administration in non-human primates of escalating intravenous doses of targeted nanoparticles containing 1 ribonucleotide reductase subunit M2 siRNA*. Proc Natl Acad Sci USA, 2007. 104(14): p. 5715-21.
21. Nanjundan, M., et al., *Amplification of MDS1/EVI1 and EVI1, located in the 3q26.2 amplicon, is associated with favorable patient prognosis in ovarian cancer*. Cancer Res, 2007. 67(7): p. 3074-84.
22. Fogel, M., et al., *L1 expression as a predictor of progression and survival in patients with uterine and ovarian carcinomas*. Lancet, 2003. 362(9387): p. 869-75.
23. Chen, T-H H, Bae, Y, and Furgeson, D Y. Intelligent biosynthetic nanobiomaterials (IBNs) for hyperthermic gene delivery. Pharm. Res. 2007 25: 683-691.
24. Bae, Y, Buresh, R A, Williamson, T P, Chen T-H H, and Furgeson, D Y. Intelligent biosynthetic nanobiomaterials for hyperthermic combination chemotherapy and thermal drug targeting of HSP90 inhibitor geldanamycin. J. Controlled Release 2007 122: 16-23.
25. Lee, S. M.; Lee, E. J.; Hong, H. Y.; Kwon, M. K.; Kwon, T. H.; Choi, J. Y.; Park, R. W.; Kwon, T. G.; Yoo, E. S.; Yoon, G. S.; Kim, I. S.; Ruoslahti, E.; Lee, B. H. Targeting bladder tumor cells in vivo and in the urine with a peptide identified by phage display. *Mol. Cancer Res.* 2007, 5, 11-9.
26. Shukla, G. S.; Krag, D. N. Selection of tumor-targeting agents on freshly excised human breast tumors using a phage display library. *Oncol. Rep.* 2005, 13, 757-64. cells.
27. Bedi, D., Musacchio, T., Fagbohum, O. A., Gillespie, J. W., Deinnocentes, P., Bird, R. C., Bookbinder, L., Torchilin, V. P., and Petrenko, V. A. Delivery of siRNA into breast cancer cells via phage-fusion protein-targeted liposomes. Nanomedicine (2011)
28. Hibino S, Shibuya M, Engbring J A, Mochizuki M, Nomizu M, Kleinman H K. Identification of an active site on the laminin alpha5 chain globular domain that binds to CD44 and inhibits malignancy. Cancer Res 2004; 64:4810-4816.
29. Zhang, Y.; Chen, J.; Hu, Z.; Hu, D.; Pan, Y.; Ou, S.; Liu, G.; Yin, X.; Zhao, J.; Ren, L.; Wang, J. Panning and identification of a colon tumor binding peptide from a phage display peptide library. *J. Biomol. Screening* 2007, 12, 429-435.
30. Kelly, K. A.; Jones, D. A. Isolation of a colon tumor specific binding peptide using phage display selection. *Neoplasia* 2003, 5, 437-44.
31. Pierschbacher M D, Ruoslahti E. Cell attachment activity of fibronectin can be duplicated by small synthetic fragments of the molecule. Nature 1984; 309:30-33.
32. Du, B.; Qian, M.; Zhou, Z.; Wang, P.; Wang, L.; Zhang, X.; Wu, M.; Zhang, P.; Mei, B. In vitro panning of a targeting peptide to hepatocarcinoma from a phage display peptide library. *Biochem. Biophys. Res. Commun* 2006, 342, 956-62.
33. Iwamoto Y, Robey F A, Graf J, Sasaki M, Kleinman H K, Yamada Y, Martin G R. YIGSR, a synthetic laminin pentapeptide, inhibits experimental metastasis formation. Science 1987; 238:1132-1134.
34. Oyama, T.; Sykes, K. F.; Samli, K. N.; Minna, J. D.; Johnston, S. A.; Brown, K. C. Isolation of lung tumor specific peptides from a random peptide library: generation of diagnostic and cell-targeting reagents. *Cancer Lett.* 2003, 202, 219-230.

35. Hoffman, J. A.; Giraudo, E.; Singh, M.; Zhang, L.; Inoue, M.; Porkka, K.; Hanahan, D.; Ruoslahti, E. Progressive vascular changes in a transgenic mouse model of squamous cell carcinoma. *Cancer Cell* 2003, 4, 383-391.
36. Zhang, J.; Spring, H.; Schwab, M. Neuroblastoma tumor cell-binding peptides identified through random peptide phage display. *Cancer Lett* 2001, 171, 153-164.
37. Silletti, S.; Mai, F.; Sheppard, D.; Montgomery, A. M. P. Plasmin-sensitive dibasic sequences in the third fibronectin-like domain of L1 cell adhesion molecule (CAM) facilitate homomultimerization and concomitant integrin recruitment. J. Cell Biol. 2000, 149, 1485-1501.
38. Aina, O. H.; Marik, J.; Gandour-Edwards, R.; Lam, K. S. Near-Infrared Optical Imaging of Ovarian Cancer Xenografts with Novel alpha3-Integrin Binding Peptide, *Mol. Imaging* 2005, 4, 439-447.
39. Joyce, J. A.; Laakkonen, P.; Bernasconi, M.; Bergers, G.; Ruoslahti, E.; Hanahan, D. Stage-specific vascular markers revealed by phage display in a mouse model of pancreatic islet tumorigenesis. *Cancer Cell* 2003, 4, 393-403.
40. Romanov, V. I.; Durand, D. B.; Petrenko, V. A. Phage display selection of peptides that affect prostate carcinoma cells attachment and invasion. *Prostate* 2001, 47, 239-251.
41. Newton. J. R.; Kelly, K. A.; Mahmood, U.; Weissleder, R.; Deutscher, S. L. In vivo selection of phage for the optical imaging of PC-3 human prostate carcinoma in mice. Neoplasia. 8, 772-780.
42. DeRoock, I. B.; Pennington, M. E.; Sroka, T. C.; Lam, K. S.; Bowden, G. T.; Bair, E. L.; Cress, A. E. Synthetic peptides inhibit adhesion of human tumor cells to extracellular matrix proteins. *Cancer Res.* 2001, 61, 3308-3313.
43. Sroka, T. C.; Marik, J.; Pennington, M. E.; Lam, K. S.; Cress, A. E. The minimum element of a synthetic peptide required to block prostate tumor cell migration. *Cancer Biol. Ther.* 2006, 5, 1556-1562.

What is claimed is:

1. An isolated polypeptide comprising an assembly domain (AD), a cell targeting domain (CTD), and a nucleic acid binding domain (NBD), wherein the isolated polypeptide comprises SEQ ID No. 56.

2. The polypeptide of claim 1, further comprising a drug binding domain (DBD).

3. The polypeptide of claim 1, wherein the nucleic acid binding domain (NBD) binds to a siRNA molecule.

4. The peptide of claim 1, wherein the NBD comprises a cationic domain.

5. The polypeptide of claim 2, wherein the DBD binds a conventional or investigational drug.

6. An isolated polypeptide comprising an assembly domain (AD), a cell targeting domain (CTD), and a nucleic acid binding domain (NBD), wherein the CTD comprises SEQ ID No. 19.

7. An isolated cDNA polynucleotide comprising a nucleotide sequence that encodes the polypeptide of claim 1, wherein the isolated polynucleotide comprises SEQ ID No. 55.

8. A recombinant expression construct comprising the polynucleotide of claim 7.

9. An isolated host cell comprising the polynucleotide of claim 7.

10. A nanoparticle comprising one or more polypeptides according to claim 1, wherein the nanoparticle assembles in solution.

11. The nanoparticle of claim 10, further comprising a drug agent.

12. The nanoparticle of claim 11, wherein the drug agent is a siRNA, shRNA, miRNA, antisense nucleic acid, single-stranded nucleic acid, double-stranded nucleic acid, DNA expression vector, RNA expression vector, plasmid, viral vector, oligonucleotide, or chemical compound.

13. A method of targeting a drug agent to a target cell, comprising:
  obtaining one or more polypeptides comprising an assembly domain (AD), a nucleotide binding domain (NBD), and a cell targeting domain (CTD);
  contacting the drug agent with the NBD of one or more polypeptides;

assembling the AD of one or more polypeptides to generate an assembled polypeptide;

contacting the assembled polypeptide with the target cell; and contacting the CTD of the assembled polypeptide with a biological molecule present outside of the target cell, wherein one or more of the polypeptides comprises SEQ ID No. 56.

14. The method of claim 13, wherein the drug agent comprises a siRNA, shRNA, miRNA, antisense nucleic acid, single-stranded nucleic acid, double-stranded nucleic acid, DNA expression vector, RNA expression vector, plasmid, viral vector, oligonucleotide, or chemical compound.

15. The method of claim 13, wherein the cell comprises a tumor cell.

16. The method of claim 15, wherein the tumor cell is a human bladder cell, a human breast cell, a human colon cell, a human liver cell, a human lung cell, a human neuroblastoma cell, a human ovarian cell, a human pancreatic cell, a human prostate cell, or a human skin cell.

17. The nanoparticle of claim 10, wherein the nanoparticle assembles in solution when combined with nucleic acid.

18. An isolated cDNA polynucleotide encoding the polypeptide of claim 1.

19. An isolated cDNA polynucleotide encoding the polypeptide of claim 6.

* * * * *

SEQUENCE LISTING

```
<160> NUMBER OF SEQ ID NOS: 66

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Cys Ser Asn Arg Asp Ala Arg Arg Cys
1               5

<210> SEQ ID NO 2
<211> LENGTH: 20
<212> TYPE: PRT
<213> ORGANISM: Artificial Sequence
<220> FEATURE:
<223> OTHER INFORMATION: Synthetic

<400> SEQUENCE: 2

Val Ser Gln Thr Met Arg Gln Thr Ala Val Pro Leu Leu Trp Phe Trp
1               5                   10                  15

Thr Gly Ser Leu
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic

<400> SEQUENCE: 3

Met Thr Val Cys Asn Ala Ser Gln Arg Gln Ala His Ala Gln Ala Thr
1               5                   10                  15

Ala Val Ser Leu
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic
```

```
<400> SEQUENCE: 4

Arg Gly Asp Leu Ala Thr Leu Arg Gln Leu Ala Gln Glu Asp Gly Val
1               5                   10                  15

Val Gly Val Arg
            20

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Asp Met Pro Gly Thr Val Leu Pro
1               5

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Arg Leu Val Ser Tyr Asn Gly Ile Ile Phe Phe Leu Lys
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Val His Leu Gly Tyr Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Cys Pro Ile Glu Asp Arg Pro Met Cys
1               5

<210> SEQ ID NO 9
<211> LENGTH: 3
<212> TYPE: PRT
<213> ORGANISM: Artificial Sequence
<220> FEATURE:
<223> OTHER INFORMATION: Synthetic

<400> SEQUENCE: 9

Arg Gly Asp
1

<210> SEQ ID NO 10
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 10

Thr Ala Cys His Gln His Val Arg Met Val Arg Pro
1               5                  10

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

Tyr Ile Gly Ser Arg Ala
1               5

<210> SEQ ID NO 12
<211> LENGTH: 20
<212> TYPE: PRT
<213> ORGANISM: Artificial Sequence
<220> FEATURE:
<223> OTHER INFORMATION: Synthetic

<400> SEQUENCE: 12

Val Ser Gln Thr Met Arg Gln Thr Ala Val Pro Leu Leu Trp Phe Trp
1               5                  10                  15

Thr Gly Ser Leu
            20

<210> SEQ ID NO 13
<211> LENGTH: 20
<212> TYPE: PRT
<213> ORGANISM: Artificial Sequence
<220> FEATURE:
<223> OTHER INFORMATION: Sythetic

<400> SEQUENCE: 13

Met Thr Val Cys Asn Ala Ser Gln Arg Gln Ala His Ala Gln Ala Thr
1               5                  10                  15

Ala Val Ser Leu
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Arg Gly Asp Leu Ala Thr Leu Arg Gln Leu Ala Gln Glu Asp Gly Val
1               5                  10                  15

Val Gly Val Arg
            20

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Cys Gly Lys Arg Lys
1               5
```

```
<210> SEQ ID NO 16
<211> LENGTH: 5
<212> TYPE: PRT
<213> ORGANISM: Artificial Sequence
<220> FEATURE:
<223> OTHER INFORMATION: Synthetic

<400> SEQUENCE: 16

Cys Asp Thr Arg Leu
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 17

Asn Gly Xaa Gly Xaa Xaa
1               5

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Val Pro Trp Met Glu Pro Ala Tyr Gln Arg Phe Leu
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Synthetic

<400> SEQUENCE: 19

Gly Ser Gln Arg Lys His Ser Lys Arg His Ile His Lys Asp His Val
1               5                   10                  15

<210> SEQ ID NO 20
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 20

Asp Gly Xaa Gly Xaa Xaa
1               5
```

```
<210> SEQ ID NO 21
<211> LENGTH: 3
<212> TYPE: PRT
<213> ORGANISM: Artificial Sequence
<220> FEATURE:
<223> OTHER INFORMATION: Synthetic

<400> SEQUENCE: 21

Lys Ala Ala
1

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Asp Pro Arg Ala Thr Pro Gly Ser
1               5

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Ile Ala Gly Leu Ala Thr Pro Gly Trp Ser His Trp Leu Ala Leu
1               5                   10                  15

<210> SEQ ID NO 24
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: Xaa can be any naturally occurring amino acid

<400> SEQUENCE: 24

Asp Asn Arg Ile Arg Leu Gln Ala Lys Xaa Xaa
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: Xaa can be any naturally occurring amino acid

<400> SEQUENCE: 25

Leu Asn Asn Ile Val Ser Val Asn Gly Arg His Xaa
1               5                   10

<210> SEQ ID NO 26
<211> LENGTH: 10
<212> TYPE: PRT
<213> ORGANISM: Artificial Sequence
<220> FEATURE:
```

```
<223> OTHER INFORMATION: Synthetic

<400> SEQUENCE: 26

Lys Ile Lys Met Val Ile Ser Trp Lys Gly
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Cys Ser Arg Pro Arg Arg Ser Glu Cys
1               5

<210> SEQ ID NO 28
<211> LENGTH: 27
<212> TYPE: DNA
<213> ORGANISM: Artificial Sequence
<220> FEATURE:
<223> OTHER INFORMATION: Synthetic

<400> SEQUENCE: 28
tgctctaacc gtgacgcgcg tcgttgc                                          27

<210> SEQ ID NO 29
<211> LENGTH: 60
<212> TYPE: DNA
<213> ORGANISM: Artificial Sequence
<220> FEATURE:
<223> OTHER INFORMATION: Synthetic

<400> SEQUENCE: 29
gtttctcaga ccatgcgtca gaccgcggtt ccgctgctgt ggttctggac cggttctctg      60

<210> SEQ ID NO 30
<211> LENGTH: 60
<212> TYPE: DNA
<213> ORGANISM: Artificial Sequence
<220> FEATURE:
<223> OTHER INFORMATION: Synthetic

<400> SEQUENCE: 30
atgaccgttt gcaacgcgtc tcagcgtcag gcgcacgcgc aggcgaccgc ggtttctctg      60

<210> SEQ ID NO 31
<211> LENGTH: 60
<212> TYPE: DNA
<213> ORGANISM: Artificial Sequence
<220> FEATURE:
<223> OTHER INFORMATION: Synthetic

<400> SEQUENCE: 31
cgtggtgacc tggcgaccct gcgtcagctg gcgcaggaag acggtgttgt tggtgttcgt      60

<210> SEQ ID NO 32
<211> LENGTH: 24
<212> TYPE: DNA
<213> ORGANISM: Artificial Sequence
<220> FEATURE:
<223> OTHER INFORMATION: Synthetic

<400> SEQUENCE: 32
gacatgccgg gtaccgttct gccg                                             24
```

<210> SEQ ID NO 33
<211> LENGTH: 39
<212> TYPE: DNA
<213> ORGANISM: Artificial Sequence
<220> FEATURE:
<223> OTHER INFORMATION: Synthetic

<400> SEQUENCE: 33
cgtctggttt cttacaacgg tatcatcttc ttcctgaaa                                39

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
gttcacctgg gttacgcgac c                                                  21

<210> SEQ ID NO 35
<211> LENGTH: 27
<212> TYPE: DNA
<213> ORGANISM: Artificial Sequence
<220> FEATURE:
<223> OTHER INFORMATION: Synthetic

<400> SEQUENCE: 35
tgcccgatcg aagaccgtcc gatgtgc                                            27

<210> SEQ ID NO 36
<211> LENGTH: 9
<212> TYPE: DNA
<213> ORGANISM: Artificial Sequence
<220> FEATURE:
<223> OTHER INFORMATION: Synthetic

<400> SEQUENCE: 36 cgtggtgac                                                                 9

<210> SEQ ID NO 37
<211> LENGTH: 36
<212> TYPE: DNA
<213> ORGANISM: Artificial Sequence
<220> FEATURE:
<223> OTHER INFORMATION: Synthetic

<400> SEQUENCE: 37
accgcgtgcc accagcacgt tcgtatggtt cgtccg                                  36

<210> SEQ ID NO 38
<211> LENGTH: 18
<212> TYPE: DNA
<213> ORGANISM: Artificial Sequence
<220> FEATURE:
<223> OTHER INFORMATION: Synthetic

<400> SEQUENCE: 38
tacatcggtt ctcgtgcg                                                      18

<210> SEQ ID NO 39
<211> LENGTH: 60
<212> TYPE: DNA
<213> ORGANISM: Artificial Sequence
<220> FEATURE:
<223> OTHER INFORMATION: Synthetic

```
<400> SEQUENCE: 39
gtttctcaga ccatgcgtca gaccgcggtt ccgctgctgt ggttctggac cggttctctg    60

<210> SEQ ID NO 40
<211> LENGTH: 60
<212> TYPE: DNA
<213> ORGANISM: Artificial Sequence
<220> FEATURE:
<223> OTHER INFORMATION: Synthetic

<400> SEQUENCE: 40
atgaccgttt gcaacgcgtc tcagcgtcag gcgcacgcgc aggcgaccgc ggtttctctg    60

<210> SEQ ID NO 41
<211> LENGTH: 60
<212> TYPE: DNA
<213> ORGANISM: Artificial Sequence
<220> FEATURE:
<223> OTHER INFORMATION: Synthetic

<400> SEQUENCE: 41
cgtggtgacc tggcgaccct gcgtcagctg gcgcaggaag acggtgttgt tggtgttcgt    60

<210> SEQ ID NO 42
<211> LENGTH: 15
<212> TYPE: DNA
<213> ORGANISM: Artificial Sequence
<220> FEATURE:
<223> OTHER INFORMATION: Synthetic

<400> SEQUENCE: 42
tgcggtaaac gtaaa                                                     15

<210> SEQ ID NO 43
<211> LENGTH: 15
<212> TYPE: DNA
<213> ORGANISM: Artificial Sequence
<220> FEATURE:
<223> OTHER INFORMATION: Synthetic

<400> SEQUENCE: 43
tgcgacaccc gtctg                                                     15

<210> SEQ ID NO 44
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (13)..(18)
<223> OTHER INFORMATION: n is a, c, g, or t

<400> SEQUENCE: 44
aacggtnnng gtnnnnnn                                                  18

<210> SEQ ID NO 45
<211> LENGTH: 36
<212> TYPE: DNA
<213> ORGANISM: Artificial Sequence
<220> FEATURE:
<223> OTHER INFORMATION: Synthetic
```

```
<400> SEQUENCE: 45
gttccgtgga tggaaccggc gtaccagcgt ttcctg                                  36

<210> SEQ ID NO 46
<211> LENGTH: 48
<212> TYPE: DNA
<213> ORGANISM: Artificial Sequence
<220> FEATURE:
<223> OTHER INFORMATION: Synthetic

<400> SEQUENCE: 46
ggttctcagc gtaaacactc taaacgtcac atccacaaag accacgtt                     48

<210> SEQ ID NO 47
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (13)..(18)
<223> OTHER INFORMATION: n is a, c, g, or t

<400> SEQUENCE: 47
gacggtnnng gtnnnnnn                                                      18

<210> SEQ ID NO 48
<211> LENGTH: 9
<212> TYPE: DNA
<213> ORGANISM: Artificial Sequence
<220> FEATURE:
<223> OTHER INFORMATION: Synthetic

<400> SEQUENCE: 48 aaagcggcg                                                                 9

<210> SEQ ID NO 49
<211> LENGTH: 24
<212> TYPE: DNA
<213> ORGANISM: Artificial Sequence
<220> FEATURE:
<223> OTHER INFORMATION: Synthetic

<400> SEQUENCE: 49
gacccgcgtg cgaccccggg ttct                                               24

<210> SEQ ID NO 50
<211> LENGTH: 45
<212> TYPE: DNA
<213> ORGANISM: Artificial Sequence
<220> FEATURE:
<223> OTHER INFORMATION: Synthetic

<400> SEQUENCE: 50
atcgcgggtc tggcgacccc gggttggtct cactggctgg cgctg                        45

<210> SEQ ID NO 51
<211> LENGTH: 33
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (28)..(33)
<223> OTHER INFORMATION: n is a, c, g, or t

<400> SEQUENCE: 51
gacaaccgta tccgtctgca ggcgaaannn nnn                           33

<210> SEQ ID NO 52
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(36)
<223> OTHER INFORMATION: n is a, c, g, or t

<400> SEQUENCE: 52
ctgaacaaca tcgtttctgt taacggtcgt cacnnn                        36

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53
aaaatcaaaa tggttatctc ttggaaaggt                               30

<210> SEQ ID NO 54
<211> LENGTH: 27
<212> TYPE: DNA
<213> ORGANISM: Artificial Sequence
<220> FEATURE:
<223> OTHER INFORMATION: Synthetic

<400> SEQUENCE: 54
tgctctcgtc cgcgtcgttc tgaatgc                                  27

<210> SEQ ID NO 55
<211> LENGTH: 999
<212> TYPE: DNA
<213> ORGANISM: Artificial Sequence
<220> FEATURE:
<223> OTHER INFORMATION: Synthetic

<400> SEQUENCE: 55
atgagcgggc cgggcgtggg taaaaaaaag aaaaaaaaaa agaaaggcgt gggtgttccg    60
ggcgtgggtg ttccgggtgg cgtgtgccg ggcgcaggtg ttcctggtgt aggtgtgccg   120
ggtgttggtg tgccgggtgt tggtgtacca ggtggcggtg ttccgggtgc aggcgttccg   180
ggtggcggtg tgccgggcgt gggtgttccg ggcgtgggtg ttccgggtgg cgtgtgccg   240 ggcgcaggtg ttcctggtgt aggtgtgccg ggtgttggtg tgccgggtgt tggtgtacca   300
ggtggcggtg ttccgggtgc aggcgttccg ggtggcggtg tgccgggcgt gggtgttccg   360
ggcgtgggtg ttccgggtgg cgtgtgccg ggcgcaggtg ttcctggtgt aggtgtgccg   420
ggtgttggtg tgccgggtgt tggtgtacca ggtggcggtg ttccgggtgc aggcgttccg   480
ggtggcggtg tgccgggcgt gggtgttccg ggcgtgggtg ttccgggtgg cgtgtgccg   540 ggcgcaggtg ttcctggtgt aggtgtaccg ggtgttggtg ttccgggtgt tggtgtacca   600
ggtggtggtg ttccgggtgc aggcgttccg ggtggcggtg tgccgggcgt gggtgttccg   660
```

```
ggcgtgggtg ttccgggtgg cggtgtgccg ggcgcaggtg ttcctggtgt aggtgtgccg    720
ggtgttggtg tgccgggtgt tggtgtacca ggtggcggtg ttccgggtgc aggcgttccg    780
ggtggcggtg tgccgggcgt gggtgttccg ggcgtgggtg ttccgggtgg cggtgtgccg    840
ggcgcaggtg ttcctggtgt aggtgtgccg ggtgttggtg tgccgggtgt tggtgtacca    900
ggtggcggtg ttccgggtgc aggcgttccg ggtggcggtg tgccgggcgg atctcagcgc    960
aaacactcaa aacgtcatat tcacaaggac catgtataa                           999
```

<210> SEQ ID NO 56
<211> LENGTH: 332
<212> TYPE: PRT
<213> ORGANISM: Artificial Sequence
<220> FEATURE:
<223> OTHER INFORMATION: Synthetic

<400> SEQUENCE: 56

```
Met Ser Gly Pro Gly Val Gly Lys Lys Lys Lys Lys Lys Lys Lys Gly
1               5                   10                  15

Val Gly Val Pro Gly Val Gly Val Pro Gly Gly Gly Val Pro Gly Ala
            20                  25                  30

Gly Val Pro Gly Val Gly Val Pro Gly Val Gly Val Pro Gly Val Gly
        35                  40                  45

Val Pro Gly Gly Val Pro Gly Ala Gly Val Pro Gly Gly Gly Val
    50                  55                  60

Pro Gly Val Gly Val Pro Gly Val Gly Val Pro Gly Gly Gly Val Pro
65                  70                  75                  80

Gly Ala Gly Val Pro Gly Val Gly Val Pro Gly Val Gly Val Pro Gly
                85                  90                  95

Val Gly Val Pro Gly Gly Val Pro Gly Ala Gly Val Pro Gly Gly
            100                 105                 110

Gly Val Pro Gly Val Gly Val Pro Gly Val Gly Val Pro Gly Gly Gly
        115                 120                 125

Val Pro Gly Ala Gly Val Pro Gly Val Gly Val Pro Gly Val Gly Val
    130                 135                 140

Pro Gly Val Gly Val Pro Gly Gly Gly Val Pro Gly Ala Gly Val Pro
145                 150                 155                 160

Gly Gly Gly Val Pro Gly Val Gly Val Pro Gly Val Gly Val Pro Gly
                165                 170                 175

Gly Gly Val Pro Gly Ala Gly Val Pro Gly Gly Val Pro Gly Val
            180                 185                 190

Gly Val Pro Gly Val Gly Val Pro Gly Gly Gly Val Pro Gly Ala Gly
        195                 200                 205

Val Pro Gly Gly Gly Val Pro Gly Val Gly Val Pro Gly Val Gly Val
    210                 215                 220

Pro Gly Gly Gly Val Pro Gly Ala Gly Val Pro Gly Val Gly Val Pro
225                 230                 235                 240

Gly Val Gly Val Pro Gly Val Gly Val Pro Gly Gly Gly Val Pro Gly
                245                 250                 255

Ala Gly Val Pro Gly Gly Gly Val Pro Gly Val Gly Val Pro Gly Val
            260                 265                 270

Gly Val Pro Gly Gly Gly Val Pro Gly Ala Gly Val Pro Gly Val Gly
        275                 280                 285

Val Pro Gly Val Gly Val Pro Gly Val Gly Val Pro Gly Gly Gly Val
    290                 295                 300

Pro Gly Ala Gly Val Pro Gly Gly Gly Val Pro Gly Gly Ser Gln Arg
```

```
                305                 310                 315                 320

Lys His Ser Lys Arg His Ile His Lys Asp His Val
                325                 330

<210> SEQ ID NO 57
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa can be any naturally occuring amino acid
      except proline

<400> SEQUENCE: 57

Val Pro Gly Xaa Gly
1               5

<210> SEQ ID NO 58
<211> LENGTH: 11
<212> TYPE: PRT
<213> ORGANISM: Artificial Sequence
<220> FEATURE:
<223> OTHER INFORMATION: Synthetic

<400> SEQUENCE: 58

Val Gly Lys Lys Lys Lys Lys Lys Lys Lys Gly
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic

<400> SEQUENCE: 59

Val Gly Arg Arg Arg Arg Arg Arg Arg Arg Gly
1               5                   10

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
aaggcatgtt cgcaacatcc                                                     20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
tagtcatcct cagggtttcc                                                     20

<210> SEQ ID NO 62
<211> LENGTH: 23
<212> TYPE: DNA
<213> ORGANISM: Artificial Sequence
<220> FEATURE:
<223> OTHER INFORMATION: Synthetic
```

-continued

```
<400> SEQUENCE: 62
gggaaatcgt gcgtgacatt aag                                           23

<210> SEQ ID NO 63
<211> LENGTH: 22
<212> TYPE: DNA
<213> ORGANISM: Artificial Sequence
<220> FEATURE:
<223> OTHER INFORMATION: Synthetic

<400> SEQUENCE: 63
tgtgttggcg tacaggtctt tg                                            22

<210> SEQ ID NO 64
<211> LENGTH: 44
<212> TYPE: RNA
<213> ORGANISM: Artificial Sequence
<220> FEATURE:
<223> OTHER INFORMATION: Synthetic

<400> SEQUENCE: 64
cgacuggagc acgaggacac ugacauggac ugaaggagua gaaa                    44

<210> SEQ ID NO 65
<211> LENGTH: 23
<212> TYPE: DNA
<213> ORGANISM: Artificial Sequence
<220> FEATURE:
<223> OTHER INFORMATION: Synthetic

<400> SEQUENCE: 65
cgactggagc acgaggacac tga                                           23

<210> SEQ ID NO 66
<211> LENGTH: 26
<212> TYPE: DNA
<213> ORGANISM: Artificial Sequence
<220> FEATURE:
<223> OTHER INFORMATION: Synthetic

<400> SEQUENCE: 66
ggacactgac atggactgaa ggagta                                        26
```